United States Patent
Gervais et al.

(10) Patent No.: US 11,541,403 B2
(45) Date of Patent: Jan. 3, 2023

(54) SYSTEM AND METHOD FOR FLUID DELIVERY

(71) Applicant: POLYVALOR, LIMITED PARTNERSHIP, Montreal (CA)

(72) Inventors: Thomas Gervais, Montreal (CA); Pierre-Alexandre Goyette, Montreal (CA); Etienne Boulais, Montreal (CA)

(73) Assignee: POLYVALOR, LIMITED PARTNERSHIP, Montreal (CA)

( * ) Notice: Subject to any disclaimer, the term of this patent is extended or adjusted under 35 U.S.C. 154(b) by 0 days.

(21) Appl. No.: 17/282,050

(22) PCT Filed: Oct. 1, 2019

(86) PCT No.: PCT/CA2019/051402
§ 371 (c)(1),
(2) Date: Apr. 1, 2021

(87) PCT Pub. No.: WO2020/069609
PCT Pub. Date: Apr. 9, 2020

(65) Prior Publication Data
US 2021/0316321 A1 Oct. 14, 2021

Related U.S. Application Data

(60) Provisional application No. 62/739,685, filed on Oct. 1, 2018.

(51) Int. Cl.
*B01L 3/02* (2006.01)
*B01L 3/00* (2006.01)
(Continued)

(52) U.S. Cl.
CPC ............ *B05B 1/169* (2013.01); *B01L 3/0293* (2013.01); *B01L 3/567* (2013.01);
(Continued)

(58) Field of Classification Search
None
See application file for complete search history.

(56) References Cited

U.S. PATENT DOCUMENTS

| 4,422,833 A | 12/1983 | Miller et al. |
| 6,103,479 A | 8/2000 | Taylor |

(Continued)

FOREIGN PATENT DOCUMENTS

| EP | 1595598 B1 | 7/2014 |
| KR | 20150098150 A | 8/2015 |

(Continued)

OTHER PUBLICATIONS

International Search Report and Written Opinion issued in corresponding International application No. PCT/CA2019/051402 dated Dec. 5, 2019.
(Continued)

*Primary Examiner* — Brian R Gordon
(74) *Attorney, Agent, or Firm* — BCF LLP

(57) ABSTRACT

A system and method of fluid delivery for providing a surface fluid pattern. The system includes a fluid delivery head for fluid flow therethrough. The fluid delivery head includes a fluid delivery surface having surface openings defined therein and arranged across the fluid delivery surface as a two-dimensional display. Some of the surface openings are grouped as a surface opening unit. The surface opening unit includes at least one aspiration opening through which fluid can be provided to the fluid delivery surface and at least one injection opening through which fluid can be moved away from the fluid delivery surface. The surface opening unit includes at least three surface openings positioned as a two-dimensional display and outwardly of at least one other surface opening.

11 Claims, 16 Drawing Sheets

(51) Int. Cl.
  *B05B 1/16* (2006.01)
  *G01N 35/10* (2006.01)

(52) U.S. Cl.
  CPC ... *B01L 2300/049* (2013.01); *B01L 2300/089* (2013.01); *B01L 2300/0867* (2013.01); *B01L 2400/0463* (2013.01); *B01L 2400/0487* (2013.01); *B01L 2400/0622* (2013.01); *G01N 35/1016* (2013.01); *G01N 2035/1034* (2013.01)

(56) References Cited

U.S. PATENT DOCUMENTS

| | | | |
|---|---|---|---|
| 6,488,040 | B1 | 12/2002 | De Larios et al. |
| 7,026,124 | B2 | 4/2006 | Barth et al. |
| 7,329,111 | B2 | 2/2008 | Delamarche et al. |
| 7,491,272 | B2 | 2/2009 | Delamarche et al. |
| 7,655,189 | B2 | 2/2010 | Willms et al. |
| 7,670,772 | B2 | 3/2010 | Kim et al. |
| 7,946,692 | B2 | 5/2011 | Hawkins et al. |
| 8,343,778 | B2 | 1/2013 | Yu et al. |
| 8,695,639 | B2 | 4/2014 | Delamarche et al. |
| 8,821,796 | B2 | 9/2014 | Peng |
| 9,695,985 | B2 | 7/2017 | Hodges et al. |
| 9,839,932 | B2 | 12/2017 | Uchiyama et al. |
| 2002/0092767 | A1 | 7/2002 | Bjornson et al. |
| 2002/0121529 | A1* | 9/2002 | Hoummady .......... B01L 3/0268 222/113 |
| 2002/0159919 | A1* | 10/2002 | Churchill ............. B01J 19/0046 436/180 |
| 2002/0164824 | A1 | 11/2002 | Xiao et al. |
| 2003/0072679 | A1* | 4/2003 | Johnson .............. F16K 11/0743 422/63 |
| 2004/0014238 | A1* | 1/2004 | Krug ................... B01J 19/0046 436/180 |
| 2004/0231438 | A1* | 11/2004 | Schwartz ............. B01L 3/0217 73/864.17 |
| 2005/0112606 | A1 | 5/2005 | Fuchs et al. |
| 2005/0130226 | A1 | 6/2005 | Ahn et al. |
| 2006/0093697 | A1 | 5/2006 | Delamarche et al. |
| 2010/0176089 | A1 | 7/2010 | Delamarche et al. |
| 2012/0289429 | A1 | 11/2012 | Chen et al. |
| 2014/0004264 | A1 | 1/2014 | Duerig et al. |
| 2014/0273070 | A1* | 9/2014 | Hale ....................... G01N 1/40 435/30 |
| 2016/0107159 | A1 | 4/2016 | Gong |
| 2016/0243549 | A1 | 8/2016 | Autebert et al. |
| 2017/0128961 | A1 | 5/2017 | Richardson |
| 2017/0304821 | A1 | 10/2017 | Kaigala et al. |

FOREIGN PATENT DOCUMENTS

| | | |
|---|---|---|
| TW | 586139 B | 5/2004 |
| WO | 2001088525 A1 | 11/2001 |
| WO | 2010128483 A2 | 11/2010 |
| WO | 2012056369 A1 | 5/2012 |
| WO | 2014001935 A1 | 1/2014 |
| WO | 2015132686 A1 | 9/2015 |
| WO | 2018033736 A1 | 2/2018 |

OTHER PUBLICATIONS

Juncker et al. (IBM) "Multipurpose microfluidic probe", Nature Materials, vol. 4, 2005.

Taylor et al. (IBM) "Centimeter scale surface interactions using hydrodynamic confinement", Langmuir 2016, 32, 10537-10544.

Queval et al. "Chamber and microfluidic probe for microperfusion of organotypic brain slices", Lab chip, 2010, 10, 326-334.

Lovchik et al. "Micro-immunohistochemiustry using a microfluidic probe", Lab chip, 2012, 12, 104001043.

Safavieh, Mohammadali, et al. "Two-aperture microfluidic probes as flow dipoles: Theory and applications." Scientific reports 5 (2015): 11943.

Qasaimeh, Mohammad A., Thomas Gervais, and David Juncker. "Microfluidic quadrupole and floating concentration gradient." Nature communications 2 (2011): 464.

Bazant, Martin Z. "Conformal mapping of some non-harmonic functions in transport theory." Proceedings of the Royal Society of London A: Mathematical, Physical and Engineering Sciences. vol. 460. No. 2045. The Royal Society, 2004.

* cited by examiner

SYSTEM AND METHOD FOR FLUID DELIVERY

CROSS-REFERENCE TO RELATED APPLICATIONS

The present application is a National Stage of International Application No. PCT/CA2019/051402, filed on Oct. 1, 2019, which claims priority to U.S. Provisional Application No. 62/739,685, filed on Oct. 1, 2018, each of which is incorporated herein by reference in its entirety.

FIELD

The present technology relates to systems and methods of fluid delivery, such as, but not limited to, systems and methods of fluid delivery for providing a surface fluid pattern.

BACKGROUND

Fluid delivery systems are used for applying a fluid to a surface in a controlled manner and find use across a diverse range of technologies such as biotechnology, diagnostic methods, and manufacturing processes.

Certain fluid delivery systems comprise an "open-space" microfluidic delivery system comprising a probe head having a planar surface with an injection aperture and an aspiration aperture for delivering and aspirating fluid to and from the planar surface in a controlled manner. The planar surface of the device is spaced from an oppositely facing fluid confining surface to create a gap in which the injected fluid from the fluid delivery system is delivered. Relative movement of the probe head and the fluid confining surface is required to move a confined reagent pattern to cover a surface.

It is an object of the present technology to provide alternative fluid delivery systems.

SUMMARY

Embodiments of the present technology have been developed based on developers' appreciation of certain shortcomings associated with existing fluid delivery systems.

Certain fluid delivery systems which are open microfluidic devices are described for example in U.S. Pat. No. 7,329,111, EP1595598, WO 2015/132686, Juncker et al, Nat. Mater. 4, 622-8 (2005), Multipurpose microfluidic probe, describing a two aperture probe; Qasaimeh et al, Nat. Commun. 2, 464 (2011)), Microfluidic quadrupole and floating concentration gradient describing a quadrupole probe; Autebert et al, Langmuir 30, 3640-5 (2014), Hierarchical hydrodynamic flow confinement: efficient use and retrieval of chemicals for microscale chemistry on surfaces, describing a hierarchical probe; Taylor et al, *Langmuir* 32, 10537-10544 (2016)), Centimeter-Scale Surface Interactions Using Hydrodynamic Flow Confinements, describing a dipole array.

These known fluid delivery systems may not be suitable for some fluid surface patterning uses due to certain limitations such as requiring movement of the fluid delivery probe relative to the surface on which the fluid pattern is being received, and a lack of versatility in that a specific probe head will have a limited number of fluid surface patterns that it can produce.

It is an object of the present technology to provide systems and methods of fluid delivery which alleviate or reduce at least some of the above-noted limitations.

According to certain aspects and embodiments, there are provided methods and systems for providing fluid surface patterns comprising repeating pixels of finite shapes. In certain embodiments, the fluid surface patterns have a symmetry on two planes or on more than two planes. According to certain embodiments, a fluid delivery system and method is provided which is reconfigurable to provide many different fluid surface patterns using the same hardware. According to certain embodiments, present methods and systems do not necessitate the use of an immersion fluid and/or a co-planar surface for producing hydrodynamic confinement. The fluid surface patterns can comprise one or more pixels comprising the same or different fluid phases selected from one or more of: different fluid compositions, different fluid concentrations, fluids with different temperatures, fluids with different colours, fluids with different functions, and the like. The fluid can be a liquid and/or a gas. The fluid may comprise a particulate flow within a non-flowing liquid or gas. The particles may be molecules.

From one aspect, there is provided a system of fluid delivery for providing a surface fluid pattern, the system comprising: a fluid delivery head for fluid flow therethrough, the fluid delivery head comprising: a fluid delivery surface having surface openings defined therein and arranged across the fluid delivery surface as a two-dimensional display; wherein at least some of the surface openings are grouped as a surface opening unit having at least one aspiration opening through which fluid can be provided to the fluid delivery surface and at least one injection opening through which fluid can be moved away from the fluid delivery surface, the surface opening unit comprising at least three surface openings positioned as a two-dimensional array and outwardly of at least one other surface opening. In certain embodiments, the surface opening unit has three aspiration openings positioned outwardly of an injection opening. In certain embodiments, the surface opening unit has three injection openings positioned outwardly of one or more aspiration openings. In certain embodiments, the fluid delivery surface has a plurality of surface opening units forming a repeating pattern of the surface openings across the fluid delivery surface. In certain embodiments, at least one of the plurality of surface opening units has three aspiration openings positioned outwardly of one or more injection openings. In certain embodiments, at least one of the plurality of surface opening units has three injection openings positioned outwardly of an aspiration opening.

From another aspect, there is provided a system of fluid delivery for providing a surface fluid pattern, the system comprising: a fluid delivery head for fluid flow therethrough, the fluid delivery head comprising: a fluid delivery surface having surface openings defined therein and arranged across the fluid delivery surface as a two-dimensional array; wherein at least some of the surface openings are grouped, or are defined, on the fluid delivery surface as a surface opening unit in a two-dimensional unit array, the surface opening unit having at least one aspiration opening through which fluid can be moved away from the fluid delivery surface and at least one injection opening through which fluid can be provided to the fluid delivery surface, the surface opening units being arranged in a repeating pattern of surface opening units across the fluid delivery surface.

In certain embodiments, the repeating pattern of surface opening units across the fluid delivery surface is a two-dimensional pattern. In certain embodiments, the surface opening unit has three aspiration openings positioned outwardly of an injection opening. In certain embodiments, the surface opening unit has three injection openings positioned outwardly of an aspiration opening.

The surface fluid pattern comprises pixels or elements of different fluid phases in certain embodiments which can give rise to a repeating pattern of the surface fluid pattern including repeating arrays of the pixels. The pixels and the repeating arrays of the pixels are finite in size. In certain embodiments, the fluid surface pattern is a tessellated pattern of fluid surface pattern elements which may or may not be confluent. The tessellated pattern may cover the fluid delivery surface without significant dead space.

In certain embodiments, the repeating pattern of the surface openings and/or the surface fluid pattern has one or more of a translational symmetry, a rotational symmetry or an inversion symmetry. The repeating pattern of the surface openings and/or the surface fluid pattern may have symmetry on two or more planes. The repeating pattern of the surface openings and/or the surface fluid pattern may have symmetry on more than two planes.

In certain embodiments, the surface opening unit has a two-dimensional polygon configuration on the fluid delivery surface, the two-dimensional polygon configuration having at least three vertices defining a virtual polygon perimeter, the surface opening unit comprising either one of: at least three of the aspiration openings representing the at least three vertices respectively, and at least one of the injection opening within the virtual perimeter of the two-dimensional polygon configuration, or at least three of the injection openings representing the at least three vertices respectively, and at least one of the aspiration opening within the virtual perimeter of the two-dimensional polygon configuration.

In certain embodiments, two adjacent surface opening units have at least one shared vertex associated with a single surface opening.

In certain embodiments, a given surface opening can be part of one or more surface opening units. The surface opening units can be overlapping. The surface opening units can be embedded within one another.

In certain embodiments, at least one of the aspiration openings representing the at least three vertices, and/or at least one of the injection openings representing the at least three vertices, can be modulated between a closed mode in which fluid cannot flow through the surface opening, an open mode in which fluid can flow through the surface opening, and injection opening mode (in which the surface opening functions as an injection opening), and an aspiration opening mode (in which the surface opening functions as an aspiration opening). At least one of the vertex surface openings can be turned off (i.e. modulated to a close mode).

In certain embodiments, the surface opening unit has a two-dimensional polygon configuration on the fluid delivery surface, the two-dimensional polygon configuration having at least three vertices defining a virtual polygon perimeter, the surface opening unit comprising either one of: at least three of the aspiration openings positioned along a perimeter of the virtual polygon, and at least one of the injection openings being positioned within the perimeter of the virtual polygon. Two adjacent surface opening units may have at least one shared surface opening.

The fluid can be at least one of a plurality of first fluid phase and a second fluid phase. In certain embodiments, any given surface opening can be arranged to fluidly deliver or receive the first fluid phase or the second fluid phase, or modulate between the first fluid phase and the second fluid phase.

In certain embodiments, a given surface opening is arranged to be modulated between an injection opening and an aspiration opening as a function of time.

In certain embodiments, the surface opening unit comprises at least one surface opening in the closed mode, during use.

In certain embodiments, there are provided a plurality of surface openings arranged as a repeating pattern across the fluid delivery surface, wherein during use, one or more of the surface openings of a surface opening unit are in the closed mode while one or more of the surface openings are in the open mode. This can define a new surface unit which can be arranged as a repeating pattern across the fluid delivery surface.

In certain embodiments, the two-dimensional array of the surface opening unit is one or more of: a triangular configuration; a square configuration; a rectangular configuration; a hexagonal configuration; and an annular configuration.

The two-dimensional configuration can include two or more openings within a perimeter. The annular configuration can have three or more surface openings arranged in a circular manner (rotationally symmetric) around an internal surface opening. The annular configuration can have one or more rings.

For the surface opening units in a polygon configuration, the polygon configuration is one or more of: a triangular configuration; a square configuration; a rectangular configuration; and a hexagonal configuration. Any number of surface openings between vertices can be provided.

In certain embodiments, the triangular configuration comprises three aspiration openings positioned outwardly, and in a triangular configuration, of at least one injection opening.

In certain embodiments, the square and rectangular configurations each comprise at least four aspiration openings positioned outwardly, and in a quadrilateral configuration, of at least one injection opening.

In certain embodiments, the hexagonal configuration comprises six aspiration openings positioned outwardly, and in a hexagonal configuration, of at least one injection opening.

In certain embodiments, the annular configuration comprises three or more aspiration openings positioned outwardly, and in a circular configuration, of at least one injection opening. In certain embodiments, the annular configuration comprises three or more injection openings positioned outwardly, and in a circular configuration, of at least one aspiration opening. This can provide fluid surface patterns in the shape of petals of a flower extending from the aspiration opening.

In certain embodiments, the surface opening unit comprises any of the surface openings configurations described herein, and including additional surface openings positioned outwardly of the surface opening configuration. For example, in one embodiment, there is provided a square configuration of openings having one internal surface openings, and four outer surface openings outwardly of the square configuration.

In certain embodiments, the system further comprises a spacer for spacing the fluid delivery surface from a fluid transfer surface, the spacer comprising one or more protrusions associated with the fluid delivery surface.

In certain embodiments, the system further comprises the fluid transfer surface, wherein the fluid transfer surface is one or more of: a dry surface, a wet surface, and a semi-dry surface.

The fluid transfer surface can be a biological surface, such as a tissue sample surface (paraffin embedded or frozen section, or cell culture or other). The ability to process a dry surface with the fluid surface pattern is achieved, in certain embodiments, through the finite size of the repeating pixels of the fluid surface pattern.

In certain embodiments, the system further comprises an imaging system for imaging the surface fluid pattern.

In certain embodiments, the system further comprises at least one pump (or pump system) in fluid communication with the surface openings through at least one fluid delivery port of the fluid delivery device. The pump can be a syringe pump, or any other type of pump. The pump can be any type of pump which can induce one or more of a pressure-driven flow, an electro-osmotic flow, or the like. In the case that the fluid comprises particulates within a liquid, the pump may be based on an electrophoresis fluid flow induction.

In certain embodiments, the system further comprises at least one valve for modulating fluid flow to the surface openings.

In certain embodiments, the system further comprises a controller for controlling a fluid parameter of the fluid flow through the surface openings, the fluid parameter comprising one or more of: a fluid flow rate, a fluid volume, a fluid flow duration, a flow of a fluid phase, a flow of a fluid concentration, a fluid flow cycle, a fluid flow frequency, wavelength or time, and a fluid flow concentration gradient.

The controller may comprise a processor of a computer system, and the processor is arranged to control the flow of fluid to the surface openings of the surface opening unit such that hydrodynamic configuration is achieved within the surface opening unit on the fluid delivery surface.

Hydrodynamic configuration may be achieved around two or more surface openings of the fluid delivery device by modulating net flow such that a sum of a fluid aspiration volume is more than a sum of a fluid injection volume. In certain embodiments, the net flow within a given surface opening unit is different than a total net flow of all the surface openings in the display.

In certain embodiments, the system further comprises one or more reservoirs of one or more fluid phases and/or waste reservoirs.

In certain embodiments, the fluid delivery device is a microfluidic delivery device.

In certain embodiments, one or more of the fluid delivery head and the fluid delivery surface is a single piece (mono-block) or two pieces (bi-block).

In certain embodiments, the fluid delivery surface is on a single plane.

In certain embodiments, the fluid delivery device is not a scanning fluid device. In other words, the fluid delivery device is fixed in position relative to a fluid transfer surface in order to produce a two-dimensional fluid surface pattern having repeating elements, and optionally having a symmetry on two or more planes.

In certain embodiments, there are no physical flow barriers between any of the surface openings on the fluid delivery surface.

In certain other embodiments, at least one physical flow barrier is provided on the fluid delivery surface. The flow barrier may extend between any of the surface openings of the fluid delivery surface, or may be positioned outwardly of the surface openings, towards at or a perimeter of the fluid delivery surface. The flow barrier may be finite or infinite with respect to the flow's reach. In certain embodiments, the flow barrier is a protrusion or an indent around a perimeter of the fluid delivery surface. The flow barrier can be a capillary barrier. In certain embodiments, the physical barrier can create a "no flux" boundary condition. At least some of the surface openings may be surrounded by the at least one physical flow barrier.

In certain embodiments, there is provided a physical flow barrier on the fluid delivery surface and wherein at least some of the surface openings are formed through physical flow barrier. The physical flow barrier may thus define a chamber with in-plane openings.

In certain other embodiments, the system further comprises a positioning system for adjusting the spacing of the fluid transfer surface from the fluid delivery surface.

From another aspect, there is provided a method for providing a surface fluid pattern, the method arranged to be executed by a processor of a computer system operatively communicable with a system including a fluid delivery device having surface openings defined in a surface delivery surface of a fluid delivery head of the fluid delivery device, the method comprising: causing fluid to flow through at least some of the surface openings which are grouped as a surface opening unit, each surface opening unit having a two-dimensional array on the fluid delivery surface, wherein the causing fluid to flow comprises causing fluid to flow in the surface opening unit by simultaneously: aspirating fluid away from the fluid delivery surface through at least three surface openings positioned as a two-dimensional array and injecting fluid towards the fluid delivery surface through another surface opening which is positioned inwardly of the at least three surface openings.

In certain embodiments, the fluid delivery surface has a plurality of surface opening units forming a repeating two-dimensional pattern (display) of the surface opening units across the fluid delivery surface, the method further comprising simultaneously causing fluid to flow in the plurality of surface opening units.

In certain embodiments, the method is arranged to be executed by a processor of a computer system operatively communicable with a system including a fluid delivery device having surface openings defined in a surface delivery surface of a fluid delivery head of the fluid delivery device, the method comprising: causing fluid to flow through at least some of the surface openings which are grouped as a surface opening unit, each surface opening unit having a two-dimensional array on the fluid delivery surface, the surface opening units being arranged in a repeating two-dimensional pattern (display) across the fluid delivery surface; wherein the causing fluid to flow comprises causing fluid to flow in the surface opening units by simultaneously, within each surface opening unit, aspirating fluid away from the fluid delivery surface through at least one aspiration openings and injecting fluid towards the fluid delivery surface through at least one injection opening.

In certain embodiments, the processor is arranged to modulate the flow rate of the fluid aspiration and the flow rate of the fluid injection in one or more of the surface opening units to achieve hydrodynamic configuration of the fluid on the fluid delivery surface.

In certain embodiments, the processor is arranged to provide a flow rate of the fluid aspiration which is more than the flow rate of the fluid injection within the one or more surface opening units. In other words, a net fluid flow through the surface openings in one surface opening unit is negative.

In certain embodiments, the hydrodynamic confinement is achieved without an immersion fluid or a co-planar surface with the fluid delivery surface.

In certain embodiments, the processor is arranged to provide a net flow rate on the fluid delivery surface which is neutral or positive. In certain embodiments, the processor is arranged to provide a net flow rate on the fluid delivery surface which is not negative.

In certain embodiments, the fluid comprises two or more fluid phases, the method comprising simultaneously providing the two or more fluid phases through the injection surface openings.

In certain embodiments, the method further comprises maintaining the fluid delivery device in a static position with respect to a fluid transfer surface for generating a two-dimensional fluid surface pattern on the fluid transfer surface.

In certain embodiments, the method further comprises dynamically modulating, in the fluid flow through the surface openings, one or more of: a fluid flow rate, a fluid volume, a fluid flow duration, a flow of a fluid phase, a flow of a fluid concentration, a fluid flow cycle, a fluid flow frequency, wavelength or time, and a fluid flow concentration gradient.

In certain embodiments, the method further comprises, for a given surface opening, modulating, as a function of time, a mode of the given surface opening between one or more of: a closed mode in which fluid cannot flow through the given surface opening, an open mode in which fluid can flow through the surface opening, an injection opening mode and an aspiration opening mode.

In certain embodiments, the method further comprises producing a sequence of surface fluid patterns by: in a first sequence frame, sending instructions to the system for causing a fluid flow to the surface opening unit according to a first configuration of the mode of the surface openings; and in a second sequence frame, sending instructions to the system for causing a fluid flow to the surface opening unit according to a second configuration of the mode of the surface openings.

In certain embodiments, the surface opening unit comprises the surface openings configured as a two-dimensional polygon having at least three vertices represented by the surface openings, the method comprising modulating a given surface opening of the surface opening unit between a closed mode in which fluid cannot flow through the surface opening, and an open mode in which fluid can flow through the surface opening. Any one or more of the surface openings associated with the vertices can be turned off/closed.

In certain embodiments, the surface fluid pattern comprises a two-dimensional repeating pattern of two or more fluids, wherein the method comprises causing the fluid flow such that the surface fluid pattern surface is created substantially concurrently.

In certain embodiments, the two-dimensional repeating pattern of two or more fluids comprises repeating units of fluid surface pattern elements, the processor being arranged to modulate the fluid flow through the surface openings such that the fluid surface pattern elements are finite in size.

In certain embodiments, the dynamic adjusting is based on an analytical model having an assumption of one or more of: a system which can continually switch in real time between the surface opening configurations of injection openings and aspiration openings, and a system having an infinite number of injection opening and aspiration opening configurations.

In certain embodiments, the analytical model comprises convection and diffusion models as a function of a fluid pattern symmetry and which relates the possible configurations through spatial transformations.

From another aspect, there is provided a use of the present systems and methods for processing a biological sample. The biological sample may be a tissue sample or live cells, and the processing may comprise immunohistochemistry, cell staining, cellular pathway analysis, and drug testing, or any other processing requiring a general surface patterning of molecular probes (e.g. Oligonucleotides (Oligomers, cDNA probes, RNA probes), proteins (antibodies, ligands, surface receptors), small molecules (fluorophores, dissolved gases, metabolites), or small particles (nanoparticles, microparticles, cells). In certain embodiments, cell cultures or tissue slices can be concurrently exposed to many reagents and experimental conditions (e.g. time, duty cycle and frequency of the exposure) over a small area. In certain embodiments, micron resolution is achievable using microfabrication techniques.

Other uses of embodiments of the present technology comprise any technology area in which exposure of a surface to a simultaneous fluid pattern is required e.g. painting, chemical processing, air filtering, combustion, and manufacturing.

According to certain aspects of the method, there is provided a computer-implemented method for obtaining a desired surface fluid pattern, the method comprising, executing by a processor of a computer system, a method comprising: obtaining a two-dimensional image of an initial surface fluid pattern, applying at least one mathematical transform to the two-dimensional image to obtain the model of the desired surface fluid pattern. The initial surface fluid pattern may comprise a simple geometry. The initial surface fluid pattern may comprise a drawing, a simulation or the like.

In certain embodiments, the mathematical transformation is a function of one complex variable. The model of the desired surface fluid pattern comprises a solution for a new geometry. The method may include more than one successive conformal transforms.

Certain embodiments of the present technology provide systems and methods, whether microfluidic or otherwise, which have one or more of the following advantages: create spatially controlled surface fluid patterns that are reconfigurable in real time; create surface fluid patterns simultaneously (as well as sequentially); create surface fluid patterns that minimize dead-space; process dry surfaces; and create predictable and controllable surface fluid patterns through novel exact theoretical models on time-dependent convection and diffusion of scalars over surfaces. Fluid patterns can thus be adjusted by controlling various fluid and flow parameters through an understanding of the relationship between the various parameters and the fluid patterns.

In the context of the present specification, unless expressly provided otherwise, the words "first", "second", "third", etc. have been used as adjectives only for the purpose of allowing for distinction between the nouns that they modify from one another, and not for the purpose of describing any particular relationship between those nouns.

Implementations of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of implementations of the present technology will become apparent from the following description, the accompanying drawings and the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a better understanding of the present technology, as well as other aspects and further features thereof, reference is made to the following description which is to be used in conjunction with the accompanying drawings, where.

It should be noted that, unless otherwise explicitly specified herein, the drawings are not to scale.

DETAILED DESCRIPTION

The present technology provides methods and systems for providing fluid surface patterns. The present technology is not limited in its use, and can be used for any purpose requiring provision of a fluid pattern on a surface, whether a wet or a dry surface. The fluid can be any type of fluid, such as a liquid, and according to certain embodiments of the present technology, can comprise a plurality of different fluid phases. The different fluid phases can be selected from one or more of fluid different compositions, different fluid concentrations, fluids with different temperatures, fluids with different colours, fluids with different functions, and the like.

Examples of certain uses of the present technology include, but are not limited to, fluid surface patterns with different surface phases for use in microfluidic processes, such as: immunohistochemical processes, surface functionalization processes, local cell lysis and DNA analysis, and gradient generation, to name a few. Although embodiments of the present technology are described below in relation to microfluidic systems and methods, the present technology can also be applied to larger scale systems which may have different uses such as large scale surface patterning, such as painting, etching, local heating, or surface-based reactions including catalysis.

Broadly, the present technology relates to the provision of numerous two-dimensional fluid surface patterns, which can be tessellated patterns with minimal dead space. Certain aspects and embodiments of the technology use a plurality of independent hydrodynamic confinement zones with finite shapes in a two-dimensional array. Unlike certain known systems, the two-dimensional fluid surface patterns can be obtained in a one-step procedure in certain embodiments, as opposed to a serial procedure requiring a scanning-type process. Furthermore, a coplanar spaced surface is not required in certain embodiments of the present technology for producing the two-dimensional surface patterns.

System

Figure 1:
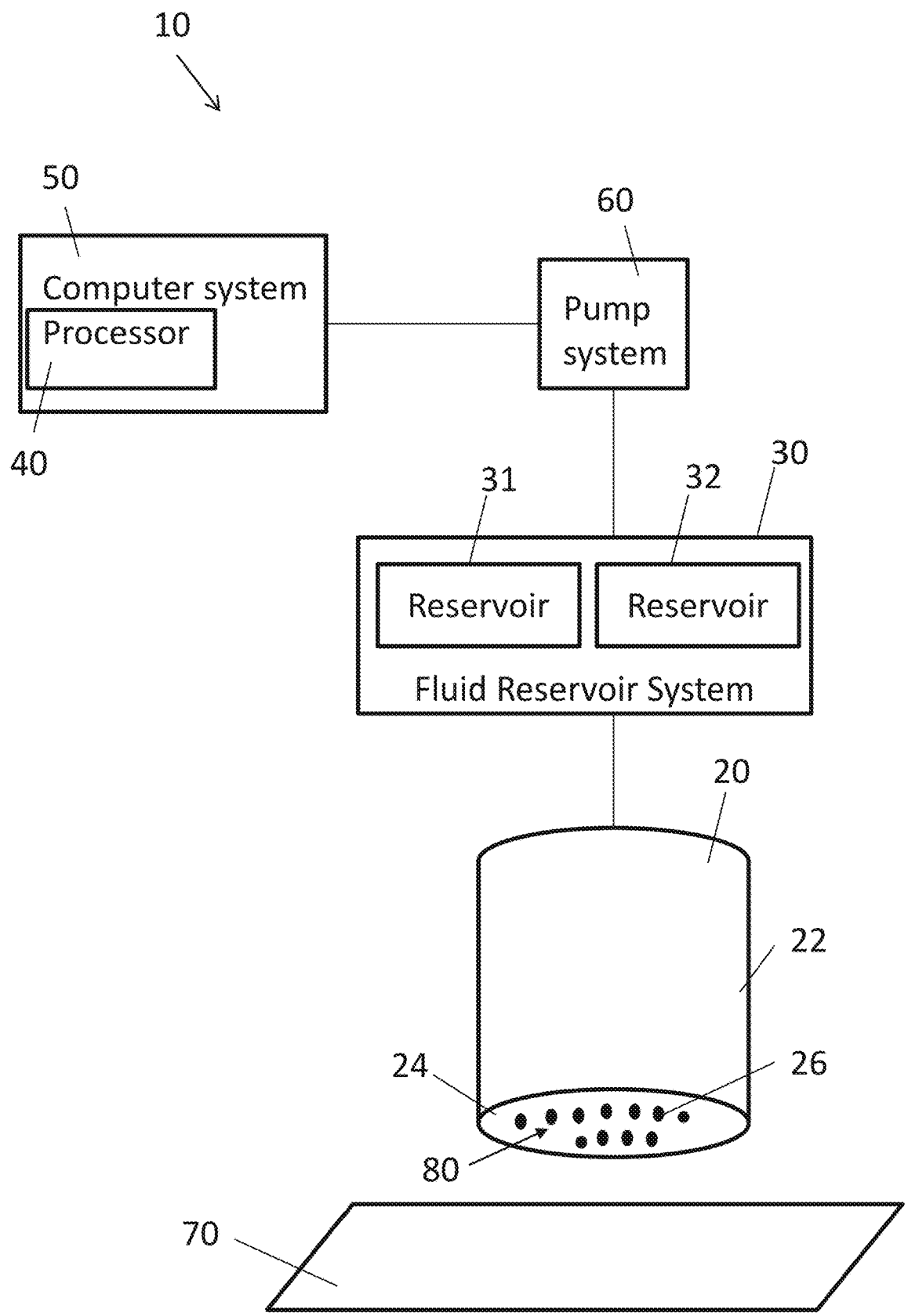
FIG. 1 illustrates a system of fluid delivery having a fluid delivery device, according to certain aspects and embodiments of the present technology.

Referring initially to FIG. 1, there is provided a system 10 for fluid delivery comprising a fluid delivery device 20 arranged for fluid flow therethrough in fluid communication with a fluid reservoir system 30 for storing fluid to be provided to the fluid delivery device 20 or to be received from the fluid delivery device 20. The system 10 includes a processor 40 of a computer system 50 communicable with a pump system 60 for controlling the flow of fluid to and from the fluid delivery device 20. Although illustrated as separate units, any one or more of the computer system 50, the pump system 60, the fluid reservoir system 30 and the fluid delivery device 20 can be incorporated as a single unit.

Fluid Delivery Device

Figures 2, 3:
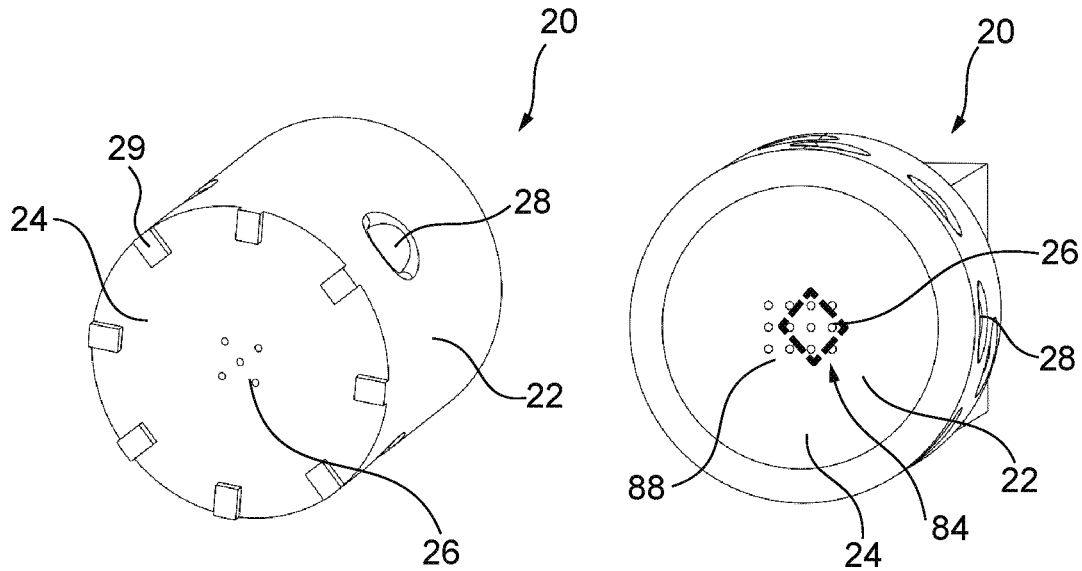
FIG. 2 illustrates a fluid delivery device of the system of FIG. 1, according to certain embodiments of the present technology.
FIG. 3 illustrates a fluid delivery device of the system of FIG. 1, according to certain other embodiments of the present technology.

With reference to FIGS. 1 and 2, the fluid delivery device 20 is a microfluidic delivery device and comprises a body 22 having a fluid delivery surface 24 with surface openings 26 defined therein. The surface openings 26 are arranged as a two-dimensional array 80 (also referred to herein as a display 80) across the fluid delivery surface 24. Fluid delivery ports 28 are formed in the body of the fluid delivery device 20 and are arranged to be in fluid communication with the surface openings 26 through channels (not shown) formed within the body 22 and in fluid communication with the fluid reservoir system 30. Tubing (not shown) may be provided, external to the body 22, and fluidly connectable to the fluid delivery ports 28 and the fluid reservoir system 30. Fluid flow through the surface openings 26 is controlled physically by valves (not shown) or the like associated with the channels and/or tubing, and in communication with the processor 40. For example, tuning valves may be provided for adjusting fluid flow through the channels (which may be microchannels), to compensate for manufacturing tolerances for example. One or more spacers 29 may be provided for spacing the fluid delivery surface 24 from a fluid transfer surface 70 (also referred to as a "fluid recipient surface 70"). The spacer 29 can comprise one or more protrusions associated with the fluid delivery surface 24, or a removeable clamp associated with one or more of the fluid delivery surface 24 and the fluid transfer surface 70.

The fluid transfer surface 70 is any surface to which the fluid surface pattern produced on the fluid delivery surface 24 can be transferred or any surface which can be processed by the fluid surface pattern. The fluid delivery surface 70, in certain embodiments, is a dry surface. In certain other embodiments, the fluid delivery surface is a wet surface. In certain embodiments, the fluid delivery surface is a tissue section, such as a paraffin embedded or frozen tissue section suitable for tissue staining or labelling.

In certain optional embodiments, the fluid delivery surface 70 is provided spaced from the fluid delivery surface 24 at a distance of from few tens to hundreds of microns, to confine the fluid in the micrometer scale, allowing a low Reynolds number and thus a laminar flow in the system.

The system 10 is arranged to inject and aspirate fluid through the surface openings 26, through application of positive and negative fluid pressure by the pump system 60, respectively. The surface openings 26 are generally multipolar: certain surface openings 26 are arranged to be aspiration surface openings 26a through which fluid is moved away from the fluid delivery surface 24, and certain surface openings 26 are arranged to be injection surface openings 26i through which fluid is moved towards the fluid delivery surface 24. Aspiration and injection surface openings 26a, 26i are also referred to herein as negative and positive surface openings, respectively.

In certain other embodiments, given surface openings 26 can function as both an aspiration surface opening 26a and an injection surface opening 26i. In these embodiments, the processor 40 is arranged to selectively modulate a mode of a given surface opening 26 between one or more of a closed mode, an open mode, an aspiration mode and an injection mode. From a practical perspective, it may be more efficient for a given surface opening 26 to switch to being a positive (injection) opening after being a negative (aspiration) opening, rather than the reverse situation, due to possible contamination of surface openings 26 with fluid that has been aspirated which may be considered as waste fluid. Whether a surface opening 26 is an aspiration opening 26a or an injection opening 26i can be arranged through a manner of fluid connection to that given surface opening 26 to one or more of the fluid reservoir system 30 and the pump system 60. In certain embodiments, a manifold (illustrated in FIG. 26 with respect to Example 6) is provided for enabling dynamic fluid connections between the surface openings 26 and the fluid reservoir system 30 which may reduce the number of pressure sources or flow sources required.

The surface openings 26 can be of any suitable size or shape for the intended use of the system 10. In certain embodiments, the surface openings 26 have a diameter of about 150 to about 250 microns. The surface openings 26 may have any suitable diameter and any suitable shape.

The fluid delivery device 20 can be formed of any appropriate material and made in any suitable manner. In certain embodiments, the fluid delivery device 20 is made by additive manufacturing of a material, such as a polymer, a metal, a ceramic or a composite.

According to certain embodiments of the present technology, enabling simultaneous fluid flow of at least two different fluid phases through the aspiration surface openings 26a and the injection surface openings 26i at appropriate fluid flow rates creates a layer of fluid on the fluid delivery surface 24 having a controllable fluid surface pattern 82, as will be described below.

Surface Opening Units and Two-Dimensional Array

According to the developers' findings, the two-dimensional array 80 of surface openings 26, comprising aspiration openings 26a and injection openings 26i, provides an ability to produce a fluid pattern 82 of the two or more fluid phases having two or more than two planes of symmetry on the fluid delivery surface 24. In certain embodiments, this is in part achieved through the provision of a two-dimensional display 80 of the surface openings 26 which are arranged to provide independent hydrodynamic confinement zones as will be explained below. At least some of the surface openings 26 are grouped as one or more surface opening units 84, with each surface opening unit 84 arranged to produce a hydrodynamic confinement in use. By grouping of the surface openings 26 is meant that the surface openings 26 of a surface opening unit 84 are arranged in a manner in which they function as a unit, regardless of their physical proximity to one another.

Broadly, the surface opening unit 84 has at least one aspiration opening 26a and at least one injection opening 26i, the surface opening unit 84 comprising at least three surface openings 26 positioned as the two-dimensional array 80 and outwardly of at least one other surface opening 26. The surface openings 26 may or may not be positioned equidistantly from one another.

Referring now to FIG. 3, an embodiment of the fluid delivery device 20 is shown in which the surface openings 26 of the display 80 are arranged in a two dimensional array, in this case a rectangular array of 3×4 surface openings 26. The surface opening unit 84 grouping of some of the surface openings 26, indicated as a dotted line, has four injection openings 26i and one aspiration opening 26a. The injection openings 26i are positioned in a two-dimensional square configuration, with each one of the injection aspirations 26i being positioned outwardly of the aspiration opening 26a. In the embodiment of FIG. 3, the display 80 of surface openings 26 are grouped as one complete surface opening unit 84, and a plurality of partial surface opening units 84.

The surface opening unit 84 can be said to have a two-dimensional polygon configuration on the fluid delivery surface 24 with four vertices 86 associated with four injection surface openings 26i. The four vertices 86 define a polygon perimeter 88 therebetween. The aspiration surface opening 26a is provided within the polygon perimeter 88 of the surface opening unit 84. In this embodiment, the polarity of a given surface opening 26 is fixed.

Figure 33:
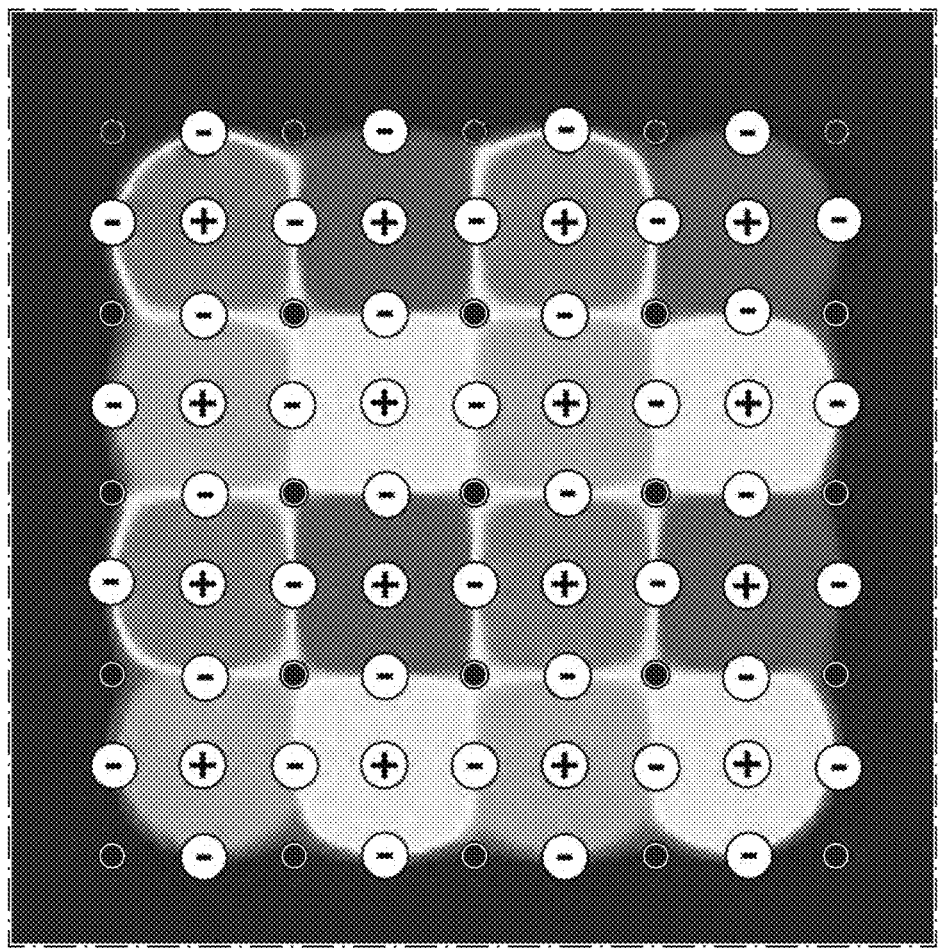
FIG. 33 shows a fluid surface pattern obtained using a fluid delivery device according to certain embodiments of the present technology.

In certain other embodiments (FIG. 33), the surface opening units 84 do not have surface openings at their vertices. As can be seen in FIG. 33, the surface openings are positioned along the perimeter of the surface opening unit 84 and within the surface opening unit 84.

Figure 4:
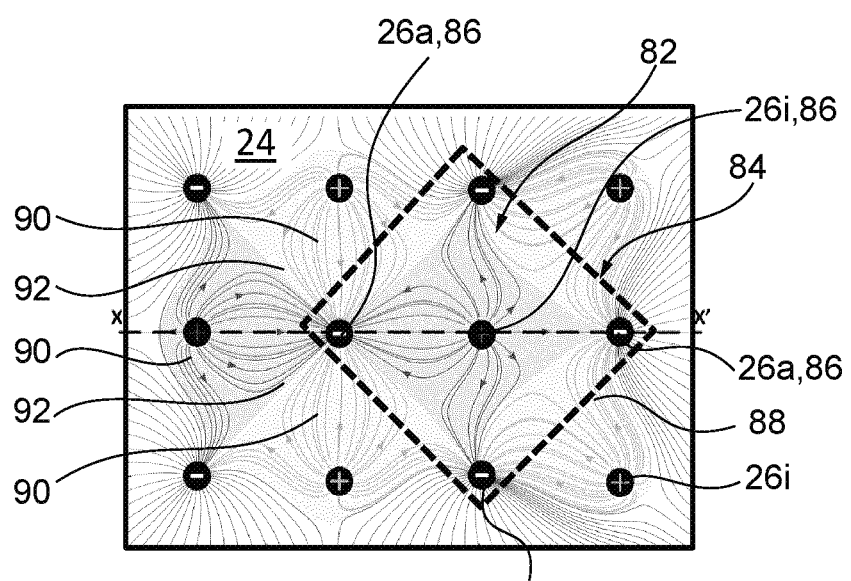
FIG. 4 illustrates a fluid delivery surface of the fluid delivery device of FIG. 3 and schematically illustrating a fluid flow direction.

As seen in FIG. 4, one of the surface patterns 82 produced by this configuration of surface opening display 80 and surface opening unit 84 and using two fluid phases (shown as a red phase and a green phase) comprises at least one pixel 90 (also referred to as "element 90") of one of the fluid phases on the fluid delivery surface 24. As represented in FIG. 4 which shows flow streamlines, the surface opening unit 84 identified as a dotted line in FIG. 3 produces the red pixel 90 in FIG. 5. Hydrodynamic configuration to produce the pixel 90 was achieved by having a total fluid aspiration rate through the aspiration openings 26a which was higher than a total fluid injection rate through the injection openings 26i of the display 80. In one embodiment the total aspiration rate was about 2.5 times higher than the total injection rate. Immersion fluid was provided around the surface openings 16.

Figure 5:
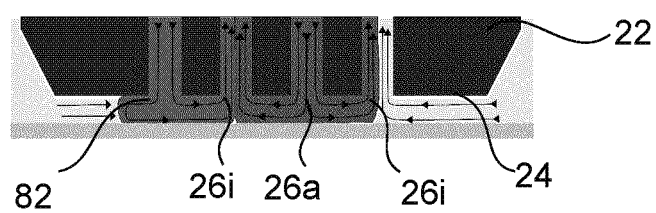
FIG. 5 is a cross-sectional view through the line x-x' of the fluid delivery device of FIG. 4.

A cross-section through the fluid delivery device 20 at the surface opening unit 84 is shown in FIG. 5, where the flow of fluid of the different fluid phases through the injection and aspiration openings 26i, 26a can be seen. A boundary 92 of the pixel 90 of the fluid surface pattern 82 of one of the fluid phases impinges on a boundary 92 of the pixel 90 of the other of the fluid phases.

The surface pattern 82 thus produced, in certain embodiments, comprises a plurality of pixels 90 of fluid phases having a symmetrical arrangement on more than two planes. The symmetry can be a translational, rotational or inversion symmetry, explained further below.

At least part of the fluid surface pattern 82 thus defined by embodiments of the present system 10 are "finite" in configuration, meaning that streamlines coming from an injection opening 26i terminate on an aspiration opening 26a, all of the streamlines located at a finite distance from the injection opening 26i. This is to be distinguished from "infinite" configuration fluid surface patterns 82, where some streamlines have one of their ends depart or terminate at "infinity", i.e. not at an aspiration opening 26a.

In other words, in certain embodiments, unlike certain known systems, certain embodiments of the present technology do not require the sum of all aspiration fluid flow rates in the surface openings 26a being higher than the sum of all injection fluid flow rates in the surface openings 26i. A "net drain", pulling the fluid toward the fluid delivery surface 24 is not required to produce at least a portion of the fluid surface pattern 82, i.e. the portion of the fluid surface pattern within the dotted square.

Figure 6:
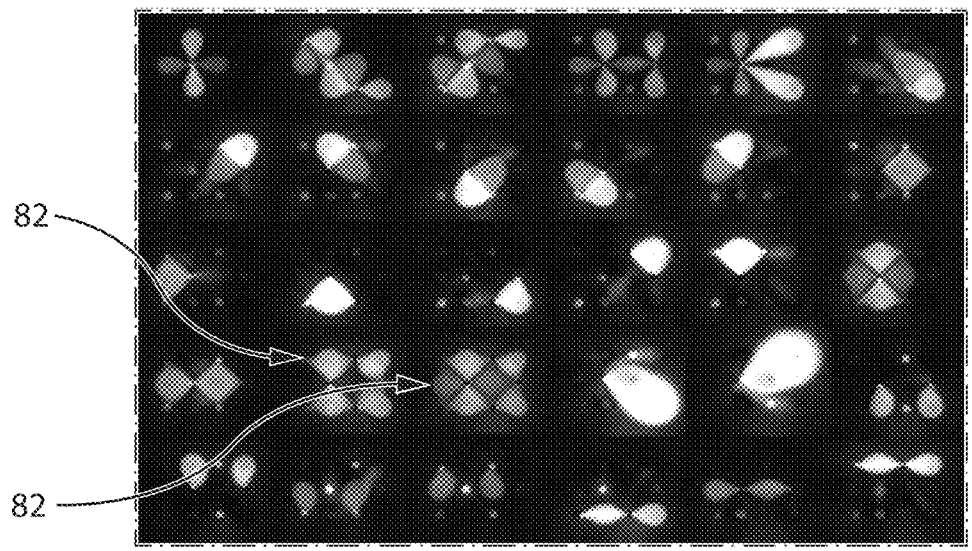
FIG. 6 shows different fluid surface patterns which can be obtained using the fluid delivery device of FIG. 3, according to certain other embodiments of the present technology.

As can be seen in FIG. 6, different fluid surface patterns 82 can be produced using the twelve-surface opening 26 display 80 arrangement of FIG. 3, and through one or more of (i) varying the polarity of a given surface opening 26, (ii) modulating a given surface opening 26 between an open mode and a closed mode, and (iii) modulating the type of fluid phase in fluid communication with the given surface opening 26. In some of the fluid surface patterns 82 of FIG. 6, the fluid surface pattern 82 is created by a single one of the surface opening unit 84 of FIG. 3. In some of the other fluid surface patterns 82 of FIG. 6, two adjacent complete or partial surface opening units 84 have been used with some of the surface openings in the closed mode.

The fluid delivery system 10 can therefore be considered as being "re-configurable" and suitable for producing a plurality of different fluid surface patterns 82. In certain embodiments, the fluid surface patterns 82 thus produced have symmetry on more than two planes.

Without being held to any theory, the number of different fluid surface patterns 82 for the display 80 can be considered to be equal to: $(n+1)^a-(n^a+1)$ where "a" is the number of the surface openings 26 in the display 80 and "n" is the number of fluid phases used. When the display 80 has given surface openings 26 which can be closed, i.e. modulated to the closed mode, the number of fluid surface patterns 82 become $(n+2)^a-((n+1)^a+2^a-1)$. When there are a large number of surface openings 26 (a>10), the number of fluid surface patterns 82 scales with $N^a$ where N includes the number of possible modes (aspiration mode, closed mode, and injection mode of n reagents). To give an order of magnitude, for a display with twelve surface openings 26 and two different fluid phases, there are $1.6 \times 10^7$ different ways to place the injection mode, the aspiration mode and the closed modes on the display 80.

It will be appreciated that if the number of surface openings 26 in the display 80 of FIG. 3 are increased, additional surface opening units 84, complete and partial, can be obtained.

Figures 7, 8:
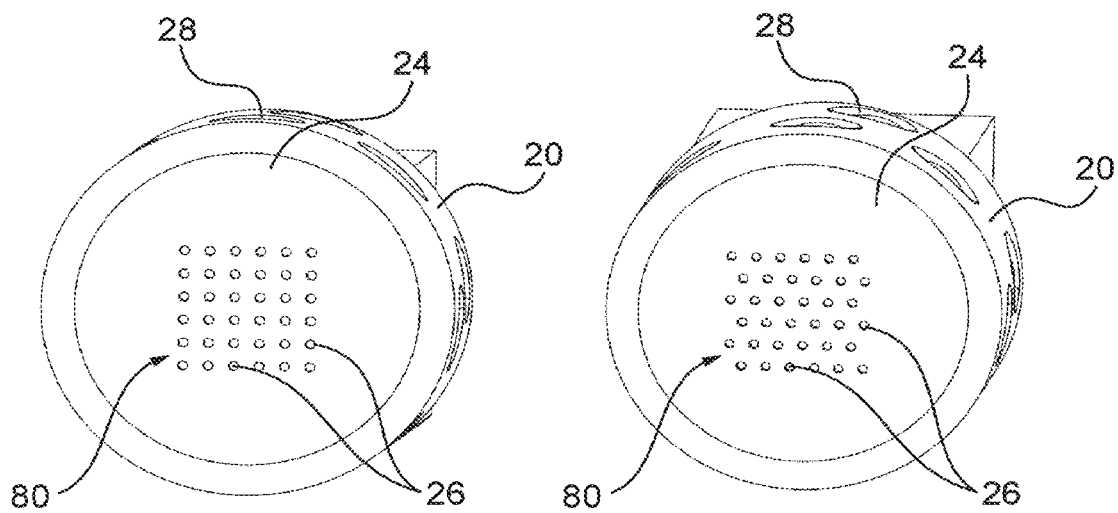
FIG. 7 illustrates certain embodiments of the fluid delivery device of the system of FIG. 1, according to certain embodiments of the present technology.
FIG. 8 illustrates certain embodiments of the fluid delivery device of the system of FIG. 1, according to certain embodiments of the present technology.

FIGS. 7 and 8 show a fluid delivery device 20 having a 6×6 surface opening 26 display 80, in which the surface openings 26 are aligned and off-set, respectively. In other embodiments, the display 80 of surface openings 26 can have any number of surface openings 26 in the aligned or off-set configurations illustrated in FIGS. 7 and 8.

It will be appreciated that within displays 80, there may be one or more surface opening units 84 having the same or different configurations.

Figures 9, 10:
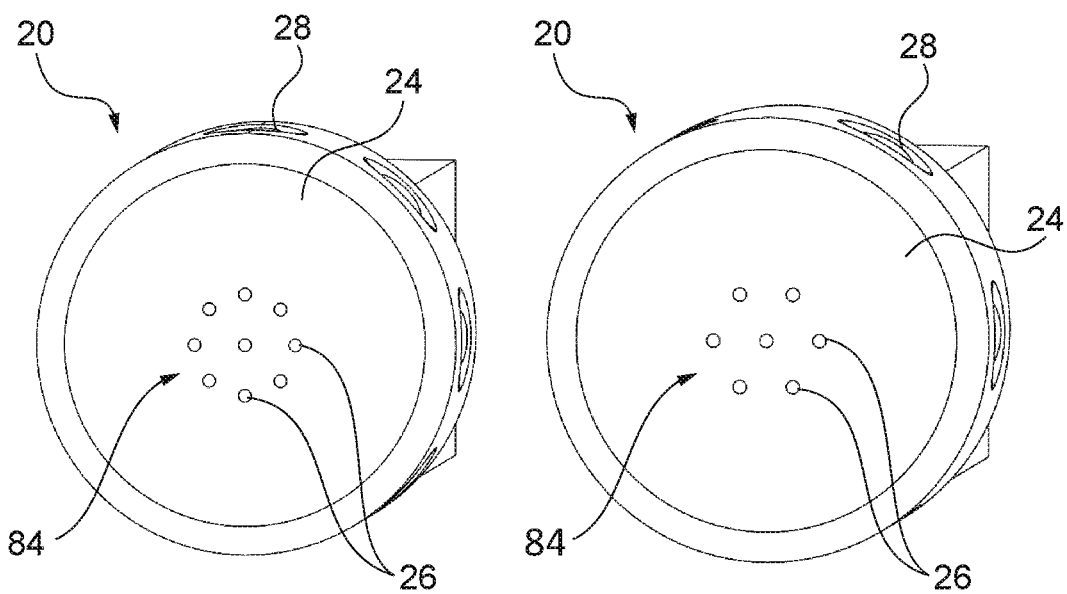
FIG. 9 illustrates certain embodiments of the fluid delivery device of the system of FIG. 1, according to certain embodiments of the present technology.
FIG. 10 illustrates certain embodiments of the fluid delivery device of the system of FIG. 1, according to certain embodiments of the present technology.
Figure 11:
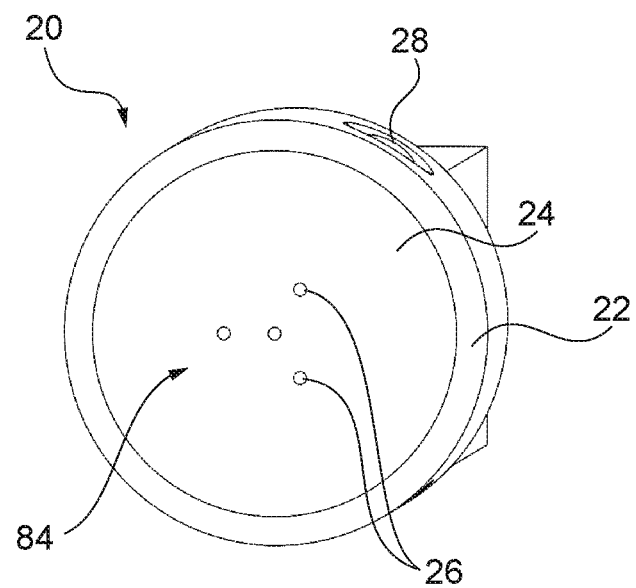
FIG. 11 illustrates certain embodiments of the fluid delivery device of the system of FIG. 1, according to certain embodiments of the present technology.

FIGS. 9-11 illustrate surface opening units 84 having a different configuration than that of FIG. 3. As also seen in FIG. 3, the surface opening units 84 comprise at least three surface openings 26 positioned as a two-dimensional array and outwardly of at least one other surface opening 26. In the embodiment of FIG. 9, there are eight surface openings 26 placed outwardly of an inner surface opening 84. In the embodiment of FIG. 10, there are six surface openings 26 placed outwardly of the inner surface opening 26. The configuration of FIG. 10 may also be referred to as a hexagonal array. In the embodiment of FIG. 11, there are three surface openings 26 placed outwardly of the inner surface opening 26. The configurations of FIGS. 9 and 10 can be referred to as an annular configuration, and the configuration of FIG. 10 as a triangular configuration.

In other embodiments, there may be provided any number of surface openings 26 arranged outwardly of the internal surface opening 26. There may also be provided one or more annular rings of surface openings 26. For multiple annular rings, the surface openings 26 in adjacent annular rings may have aligned or offset surface openings 26. There may be one or more than one inner surface opening 26.

In certain embodiments, the surface openings 26 which are positioned outwardly of the inner surface opening are all injection openings 26i, and the inner surface opening 26 is an aspiration opening 26a. In certain embodiments, the surface openings 26 which are positioned outwardly of the inner surface opening are all aspiration openings 26a, and the inner surface opening 26 is an injection opening 26i.

Other embodiments of the surface opening unit 84 are possible and which comprise three or more aspiration openings 26a forming an irregular polygon configuration, with one or more injection openings 26i within the polygon configuration.

In some embodiments of the surface opening unit 84, there are provided three or more injection openings 26a forming an irregular polygon configuration, with one or more aspiration openings 26i within the polygon configuration.

Figures 12, 13:
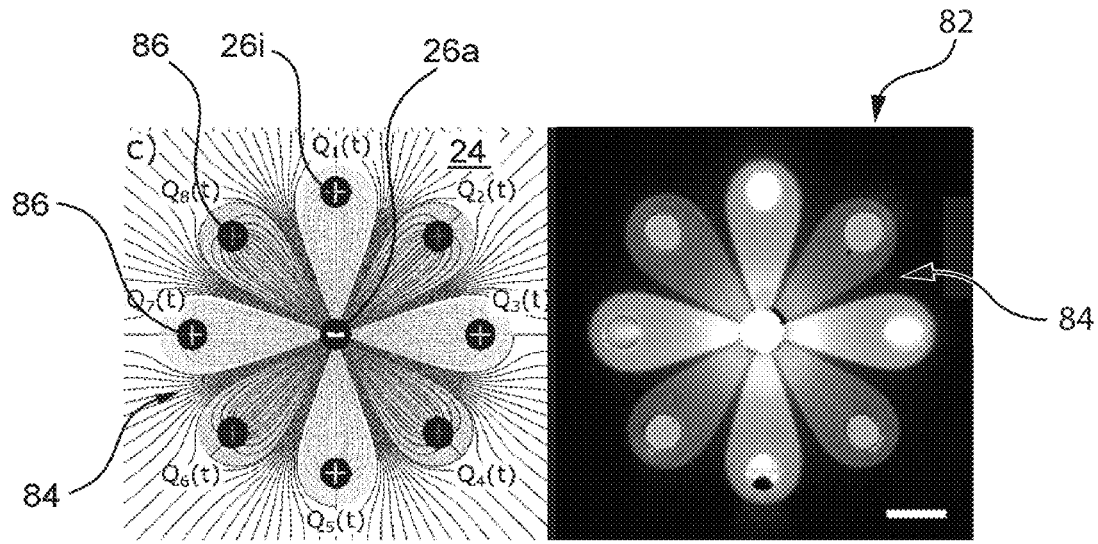
FIG. 12 illustrates a fluid delivery surface of the fluid delivery device of FIG. 9, according to certain embodiments of the present technology.
FIG. 13 shows a fluid surface pattern obtained using the fluid delivery device of FIG. 9 with the fluid delivery surface of FIG. 12, according to certain embodiments of the present technology.

FIGS. 12 and 13 illustrate one example of a fluid surface pattern 82 obtained using an embodiment of the fluid delivery device 20 and including the surface opening unit 84 of FIG. 9. FIG. 12 illustrates the flow streamlines. Eight injection openings 26i are arranged around an aspiration opening 26a. The injection openings 26i provide different fluid phases in an alternate manner. The fluid surface pattern 82 shown in FIG. 13 has rotational symmetry on at least two planes.

Figures 14, 15:
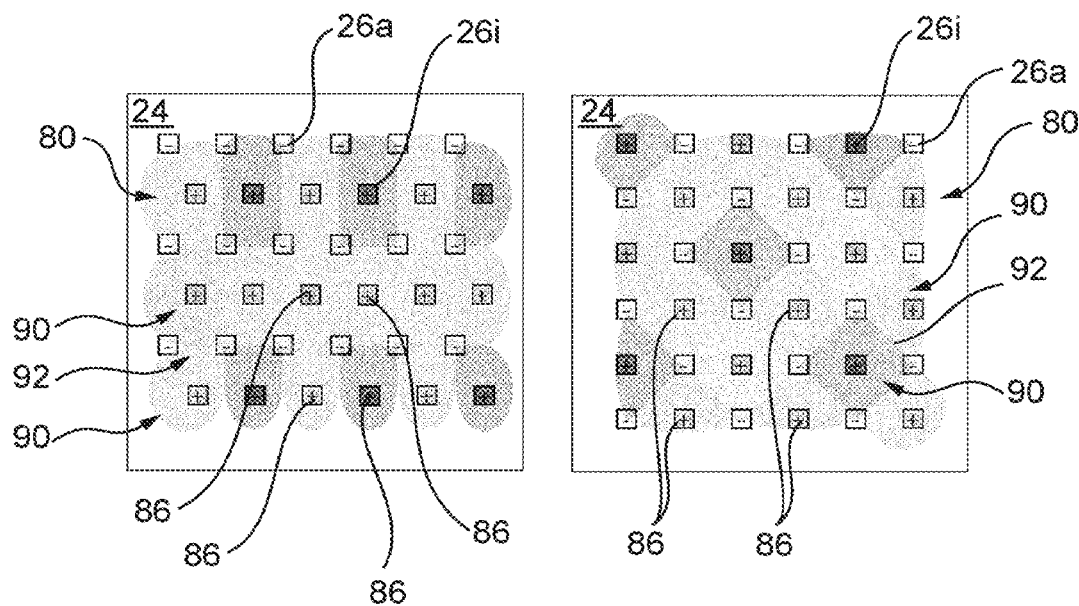
FIG. 14 shows a fluid surface pattern obtained using the fluid delivery device of FIG. 8, according to certain embodiments of the present technology.
FIG. 15 shows a fluid surface pattern obtained using the fluid delivery device of FIG. 7, according to certain embodiments of the present technology.

FIGS. 14 and 15 illustrate other examples of fluid surface patterns 82 obtained using embodiments of the fluid delivery device 20. In FIG. 14, the surface opening unit of FIG. 2 is used in the staggered configuration display 80 of FIG. 8, to achieve a fluid surface pattern 82 having translational symmetry on at least two planes. In FIG. 15, the surface opening unit 84 of FIG. 3 is used in the aligned 6×6 configuration display 80 of FIG. 7, to achieve a fluid surface pattern 82 having translational symmetry on at least two planes.

Figure 16:
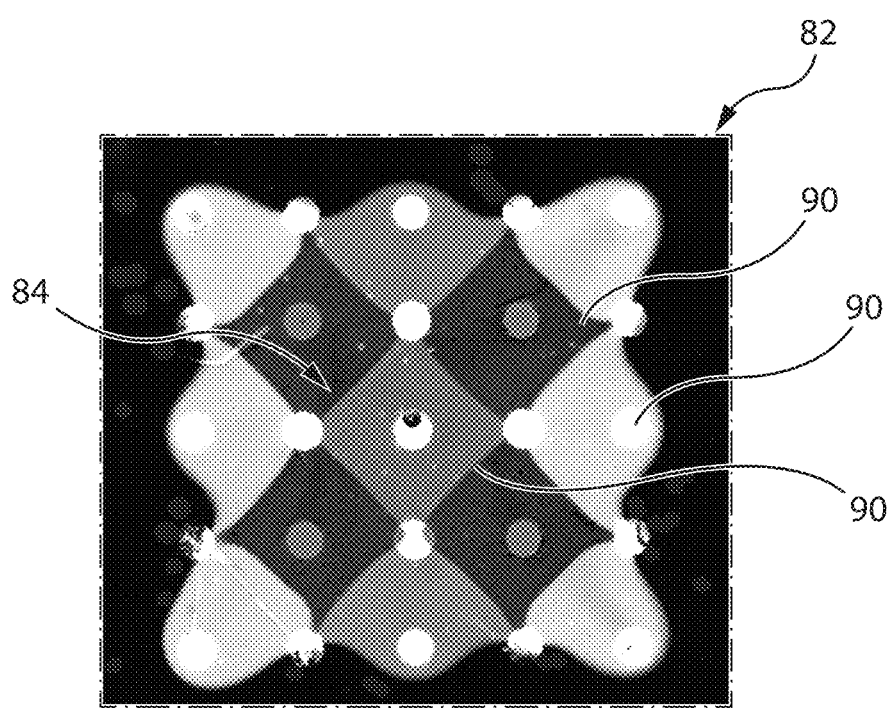
FIG. 16 shows a fluid surface pattern obtained using a fluid delivery device having a 5×5 surface opening configuration, according to certain embodiments of the present technology.

In FIG. 16, a display 80 of 5×5 surface openings 26 in an aligned array is used to create the fluid surface pattern 82 having translational symmetry on at least two planes.

As it can be appreciated, the surface opening unit 84 is used as a basic lattice to form the fluid surface pattern 82. In certain embodiments, the fluid surface pattern 82 is confluent.

It can be said that repeating surface opening units 84, of the same or different configurations, within the display 80 can provide a tessellation of both the surface opening units 84 and the fluid surface pattern 82 generated by each of the surface opening units 84.

In the above described embodiments of the fluid delivery system, there are no physical flow barriers between any of the surface openings 26 on the fluid delivery surface. The fluid surface patterns 82 can be produced by the independent hydrodynamic confinement of the individual pixels 84.

Figure 17A:
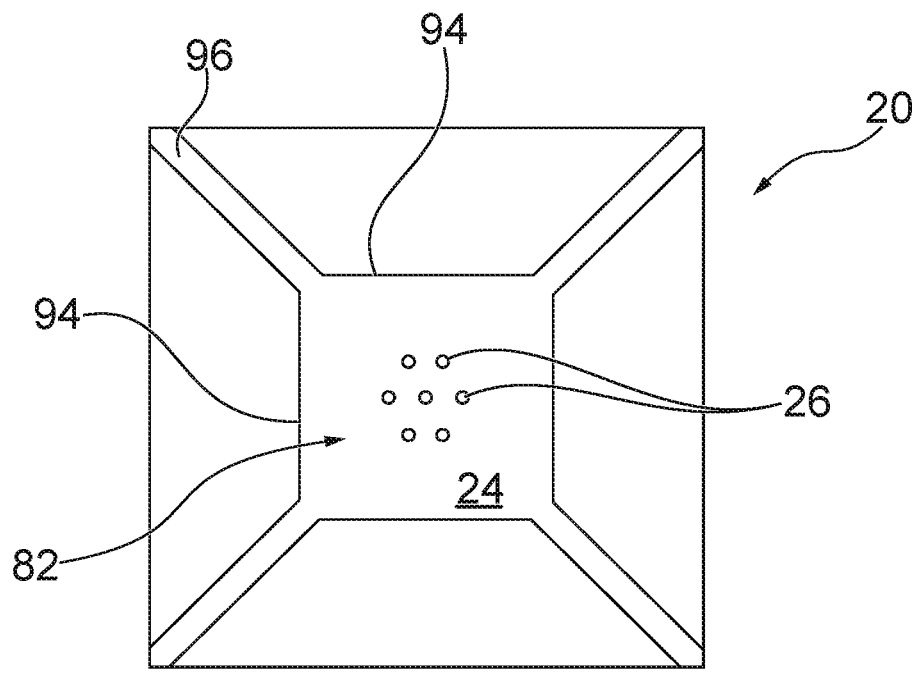
FIG. 17A is a schematic illustration of a fluid delivery device including a flow barrier, according to certain embodiments of the present technology.
Figure 17B:
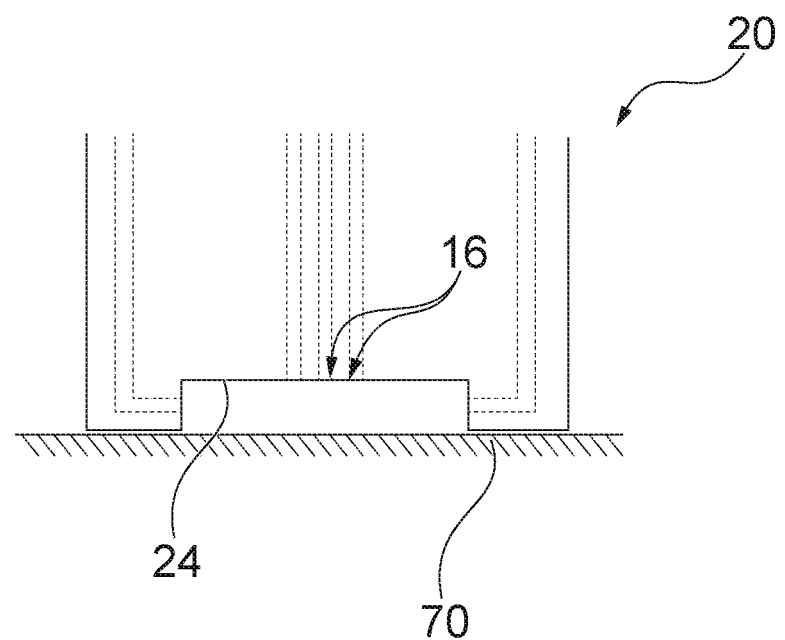
FIG. 17B is a cross-sectional view of the fluid delivery device of FIG. 17A.

However, in certain other embodiments, one or more flow barriers are provided on the fluid delivery surface 24, as illustrated in FIGS. 17A and 17B. As can be seen, a flow barrier 94 is provided around the surface opening unit 82 with channels or openings 96 provided therein. It will be appreciated that any other configuration of surface opening unit 82 or display 80 can be provided. The flow barrier 94 may comprise a wall or a block or any other type of protrusion extending from the fluid delivery surface 24.

Fluid Reservoir System

The fluid reservoir system 30 comprises one or more fluid phase reservoirs, including a first fluid reservoir 31 and a second fluid reservoir 32, arranged to store a different fluid phase. In certain embodiments, the fluid reservoir system 30 also includes one or more waste fluid reservoirs for receiving waste fluid from the fluid delivery device 20. The one or more fluid phase reservoirs and/or the one or more waste fluid reservoirs may be housed within the fluid delivery device 20.

Pump System

The pump system comprises 60 any appropriate type of pump for providing a positive pressure or a negative pressure through each surface opening 26, such as but not limited to a syringe pump. The pump is in fluid communication with the surface openings 26 through the fluid delivery port 28. In certain embodiments, at least a part of the fluid reservoir system 30 and/or the pump system 60 may be housed within the fluid delivery device 20. The aspiration openings 26 may have a common pump of the pump system 60.

Fluids

The system 10 is arranged to process fluids having different fluid phases. As mentioned above, the different fluid phases comprise one or more of: different fluid compositions, different fluid concentrations, fluids with different temperatures, fluids with different colours, fluids with different functions, fluids with different fluorescence properties, and the like.

Additional Features of System

The system 10 may further include an imaging system (not shown) for imaging the fluid surface pattern, such as an inverted fluorescence microscope, a confocal microscope, etc. The system 10 may also include a clamping system for securing the fluid delivery surface 24 relative to a fluid transfer surface 70. The clamping system may include a removable clamp associated with one or more of the fluid delivery surface 24 and the fluid transfer surface 70. The system 10 may include a positioning system for adjustably positioning the fluid delivery surface 24 relative to the fluid transfer surface 70.

Computer System

Figure 18:
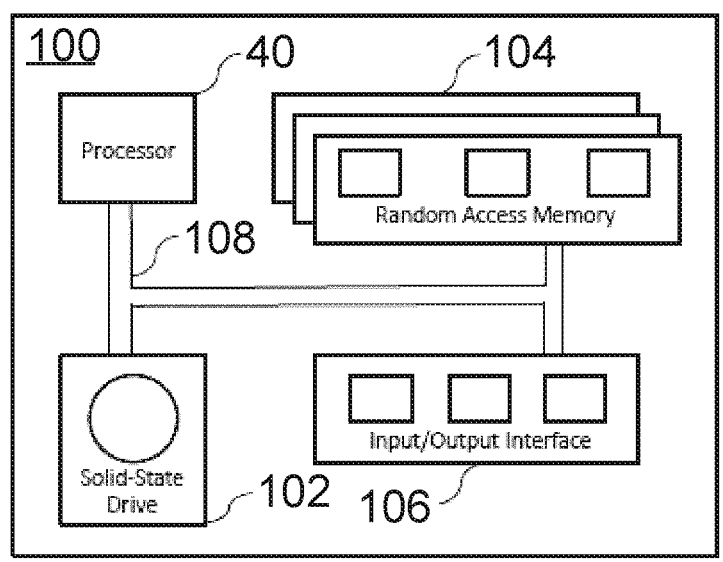
FIG. 18 shows a computing environment of the computer system of FIG. 1, according to certain other embodiments of the present technology.

Turning now to FIG. 18, certain embodiments of the computer system 50 have a computing environment 100 as illustrated schematically in FIG. 18. The computing environment 100 comprises various hardware components including one or more single or multi-core processors collectively represented by the processor 40 (also referred to herein as "controller"), a solid-state drive 102, a random-access memory 104 and an input/output interface 106. Communication between the various components of the computing environment 100 may be enabled by one or more internal and/or external buses 108 (e.g. a PCI bus, universal serial bus, IEEE 1394 "Firewire" bus, SCSI bus, Serial-ATA bus, ARINC bus, etc.), to which the various hardware components are electronically coupled.

The input/output interface 106 allows enabling networking capabilities such as wire or wireless access. As an example, the input/output interface 106 comprises a networking interface such as, but not limited to, a network port, a network socket, a network interface controller and the like. Multiple examples of how the networking interface may be implemented will become apparent to the person skilled in the art of the present technology. For example, but without being limiting, the networking interface may implement specific physical layer and data link layer standard such as Ethernet™, Fibre Channel, Wi-Fi™ or Token Ring. The specific physical layer and the data link layer may provide a base for a full network protocol stack, allowing communication among small groups of computers on the same local area network (LAN) and large-scale network communications through routable protocols, such as Internet Protocol (IP).

According to implementations of the present technology, the solid-state drive 102 stores program instructions suitable for being loaded into the random access memory 104 and executed by the processor 40 for executing methods according to certain aspects and embodiments of the present technology. For example, the program instructions may be part of a library or an application.

In this embodiment, the computing environment 100 is implemented in a generic computer system which is a conventional computer (i.e. an "off the shelf" generic computer system). The generic computer system is a desktop computer/personal computer, but may also be any other type of electronic device such as, but not limited to, a laptop, a mobile device, a smart phone, a tablet device, or a server.

In other embodiments, the computing environment 100 is implemented in a device specifically dedicated to the implementation of the present technology. For example, the computing environment 100 is implemented in an electronic device such as, but not limited to, a desktop computer/personal computer, a laptop, a mobile device, a smart phone, a tablet device, a server, specifically designed for making fluid surface patterns or for using fluid surface patterns. The electronic device may also be dedicated to operating other devices, such as the pump system 60, the fluid reservoir system 30, or the imaging system, for example.

In some alternative embodiments, the computer system 50 or the computing environment 100 is implemented, at least partially, on the pump system 60, the fluid reservoir system 30, or the imaging system, for example. In some alternative embodiments, the computer system 50 may be hosted, at least partially, on a server. In some alternative embodiments, the computer system 50 may be partially or totally virtualized through a cloud architecture.

In some embodiments, the computing environment 100 is distributed amongst multiple systems, such as the pump system 60, the fluid reservoir system 30, the imaging system, and/or the server. In some embodiments, the computing environment 100 may be at least partially implemented in another system, as a sub-system for example. In some embodiments, the computer system 50 and the computing environment 100 may be geographically distributed.

As persons skilled in the art of the present technology may appreciate, multiple variations as to how the computing environment 100 is implemented may be envisioned without departing from the scope of the present technology.

Methods

Figure 19:
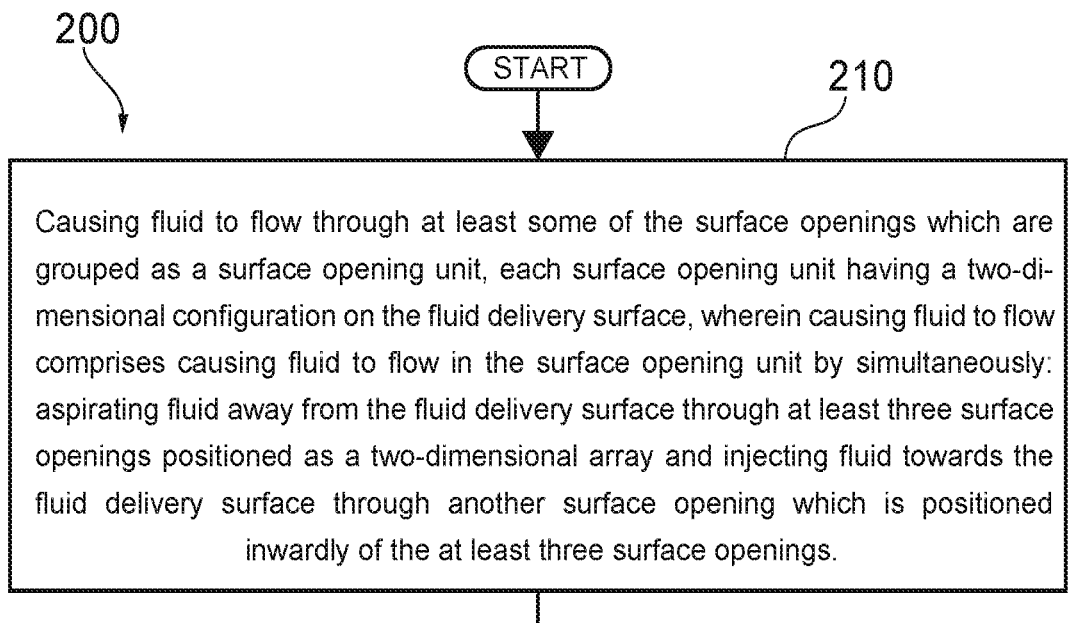
FIG. 19 is a schematic illustration of a method step of fluid delivery, according to certain aspects and embodiments of the present technology.
Figure 20:
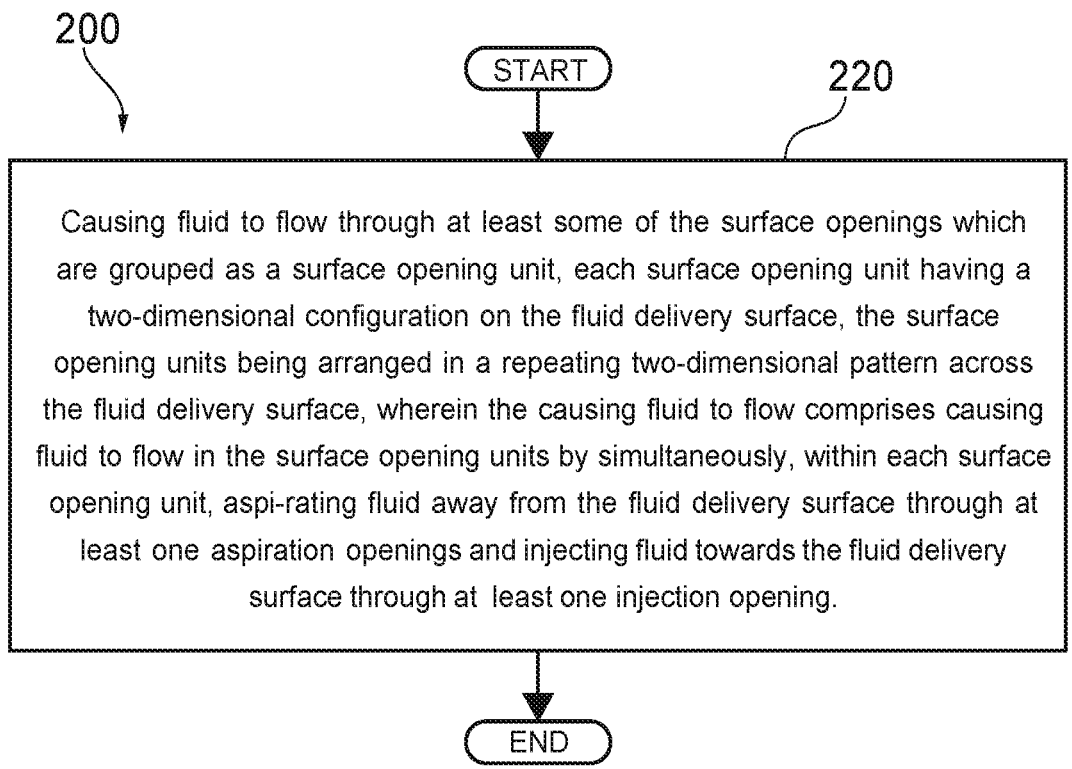
FIG. 20 is a schematic illustration of a method step of fluid delivery according to certain aspects and embodiments of the present technology

With reference now to FIGS. 19 and 20, in certain embodiments the computer system 50 is configured to execute a method 200 for providing a surface fluid pattern 82. The method 200 will now be described in further detail below. The method 200 is arranged to be executed by the processor 40 of the computer system 50 which is operatively communicable with the fluid delivery device having surface openings 26 defined in a surface delivery surface 24 of the fluid delivery device 20.

One aspect of the method 200 comprises Step 210.

Step: 210: Causing fluid to flow through at least some of the surface openings which are grouped as a surface opening unit, each surface opening unit having a two-dimensional array on the fluid delivery surface, wherein the causing fluid to flow comprises causing fluid to flow in the surface opening unit by simultaneously: aspirating fluid away from the fluid delivery surface through at least three surface openings positioned as a two-dimensional array and injecting fluid towards the fluid delivery surface through another surface opening which is positioned inwardly of the at least three surface openings.

The method 200 comprises operatively communicating with the system 10 including certain embodiments of the fluid delivery device 20. In certain embodiments, the surface openings 26 are grouped as a surface opening unit 84, each surface opening unit 84 having a two-dimensional array configuration on the fluid delivery surface 24. Fluid is caused to flow by sending instructions to the pump system 60. The fluid may comprise one or more fluid phases.

The method 200 comprises a simultaneous aspiration and injection of fluid through the surface openings 26 of the surface opening unit 84. The surface openings 26 comprise at least three aspiration openings 26a positioned as a two-dimensional array and outwardly of an injection opening 26i. The fluid delivery surface may also have a plurality of surface opening units 84 forming a repeating two-dimensional pattern of the surface opening units 84 across the fluid delivery surface 24, the method 200 further comprising simultaneously causing fluid to flow in the plurality of surface opening units 84.

In another aspect, the method 200 comprises Step 220:

Step 220: causing fluid to flow through at least some of the surface openings which are grouped as a surface opening unit, each surface opening unit having a two-dimensional configuration on the fluid delivery surface, the surface opening units being arranged in a repeating two-dimensional pattern across the fluid delivery surface, wherein the causing fluid to flow comprises causing fluid to flow in the surface opening units by simultaneously, within each surface opening unit, aspirating fluid away from the fluid delivery surface through at least one aspiration openings and injecting fluid towards the fluid delivery surface through at least one injection opening.

The method 200 comprises, in Step 230, operatively communicating with the system 10 including certain embodiments of the fluid delivery device 20. In certain embodiments, the surface openings 26 are grouped as a surface opening unit 84, each surface opening unit 84 having a two-dimensional configuration on the fluid delivery surface 24. The surface opening units 84 are positioned in a repeating two-dimensional pattern. Fluid is caused to flow by sending instructions to the pump system 60. The fluid may comprise one or more fluid phases.

The method 200 comprises a simultaneous aspiration and injection of fluid through the surface openings 26 of each of the surface opening units 84.

In certain embodiments of either of the two aspects of the method 200, which may be defined as other method steps, the processor 40 modulates the flow rate of the fluid aspiration and the flow rate of the fluid injection in one or more of the surface opening units 84 to achieve hydrodynamic configuration of the fluid on the fluid delivery surface 24. The hydrodynamic confinement can be achieved without an immersion fluid or without requiring a co-planar fluid delivery surface 70. This can provide finite fluid surface pattern elements 90 as a repeating surface fluid surface pattern 82 having more than two planes of symmetry.

The processor 50 is arranged to provide a flow rate of the fluid aspiration which is more than the flow rate of the fluid injection within the one or more surface opening units. In other words, a net fluid flow through the surface openings 26 in one surface opening unit 84 is negative. Furthermore, the processor 50 is arranged to provide a net flow rate on the fluid delivery surface 24 which is neutral or positive, and not negative.

In certain embodiments, the fluid comprises two or more fluid phases, and certain embodiments of the method 200 comprise simultaneously providing the two or more fluid phases through the injection surface openings 26i.

The surface fluid pattern 82 thus created can comprise a two-dimensional repeating pattern of the two or more fluid phases. The method 200 may comprise causing the fluid flow such that the surface fluid pattern 82 of the two or more fluid phases is created substantially concurrently. The processor 50 can be arranged to modulate the fluid flow through the surface openings 26 such that the fluid surface pattern 82 comprises the elements 90 that are finite in size.

The method 200 can further comprises dynamic fluid flow modulation steps, selected from one or more of: a fluid flow rate, a fluid volume, a fluid flow duration, a flow of a fluid phase, a flow of a fluid concentration at a given temperature, a fluid flow cycle, a fluid flow frequency, wavelength or time, and a fluid flow concentration gradient.

The dynamic modulation can occur during the creation of one or more fluid surface patterns. The various fluid flow parameters can be modulated as a function of time, or as a function of a fluid phase.

Furthermore, embodiments of the method 200 comprise, for a given surface opening, modulating, as a function of time, a function of the given surface opening 26 between one or more of: a closed mode in which fluid cannot flow through the given surface opening 26, an open mode in which fluid can flow through the surface opening 26, an injection opening mode and an aspiration opening mode.

In embodiments where there is a plurality of surface opening units 84, one or more of the surface openings 26 of each of the surface opening unit 84 can be modulated between modes, the modes comprising one or more of: a closed mode, an open mode, an injection mode, and an aspiration mode. In certain cases where the surface openings 26 of a surface opening unit 84 are arranged as a polygon, one or more of the surface openings representing the polygon vertices may be switched to the closed mode while one or more surface openings representing the polygon vertices are in the open mode.

The method 200 may further comprise producing a sequence of surface fluid patterns by: in a first sequence frame, sending instructions to the system 10 for causing a fluid flow to the surface opening unit 84 according to a first configuration of the mode of the surface openings 26; and in a second sequence frame, sending instructions to the system 10 for causing a fluid flow to the surface opening unit 84 according to a second configuration of the mode of the surface openings 26. The first and second configurations of the mode may be different to one another. There may be provided additional sequence frame steps with certain configurations of modes. By first and second configurations is meant different given surface openings 26 being in the opened and closed modes.

Such modulation between the open and closed modes, as well as the different configurations of the sequence of surface fluid patterns 82, can be considered as a stroboscope (or "c-strobe"), enabling the generation of a sequence of fluid surface patterns 82. Each sequence fluid pattern may comprise a different fluid chemical phase. Therefore, a fluid transfer surface 70, when present, could be sequentially exposed to different patterns of the fluid chemical phases. An example of this use is further described in Example 3.

The fluid delivery device 20 is maintained, in certain embodiments in a static or fixed position with respect to the fluid transfer surface 70 (if it is present), during the generation of the two-dimensional fluid surface pattern 82.

In certain embodiments, the dynamic adjusting is based on an analytical model having an assumption of one or more of: a system which can continually switch in real time between the surface opening configurations of injection openings and aspiration openings, and a system having an infinite number of injection. The analytical model can comprise convection and diffusion models as a function of a fluid pattern symmetry and which relates the possible configurations through spatial transformations (see Examples 1 and 2).

According to certain aspects of the method, there is provided a method for obtaining a desired surface fluid pattern, the method comprising obtaining a two-dimensional image of an initial surface fluid pattern, applying at least one mathematical transform to the two-dimensional image to obtain the model of the desired surface fluid pattern. The initial surface fluid pattern may comprise a simple geometry. The initial surface fluid pattern may comprise a drawing, a simulation or the like.

In certain embodiments, the mathematical transformation is a function of one complex variable. The model of the desired surface fluid pattern comprises a solution for a new geometry. The method may include more than one successive conformal transforms.

EXAMPLES

The following examples are illustrative of the wide range of applicability of the present technology and are not intended to limit its scope. Modifications and variations can be made therein without departing from the spirit and scope of the invention.

Example 1—Analytical Model for Diffusion Under the Dipolar Probe

At least a part of the Developers' current technology is based on an analytical model which they developed for diffusion under the dipolar probe, and then extended it to obtain exact flow profiles for different open microfluidic devices. In some cases, accurate approximations are instead provided based on the same model.

In analyzing the flow in the dipolar microfluidic probe, the following a dimensional system was used:

$$\vec{x} = \vec{X}/L, \vec{v} = 2\pi GL\vec{V}/Q_0, c=C/C_0.$$

where L is the interaperture distance in the probe, G is the width of the gap, $Q_0$ is the injection rate of the injection aperture and $C_0$ is the injected reagent concentration. We model the apertures as point sources and do not consider their finite radius.

Complex flow representation describes vectors in the 2D plane $\mathbb{R}^2$ as complex numbers $z=x+iy$.

Under this representation, laminar flow between two parallel plates reduces to a potential flow akin to a 2-dimensional electric field, named a Hele-Shaw flow. In this situation, the flow is completely characterized by the complex potential 15

$$\Phi = \Sigma_i q_i \log(z-z_i) \quad (1)$$

where each point-like aperture is located at position $z_i$ and has flow rate $q_i$.

One useful feature of the complex potential $\Phi=\phi+i\psi$ is that its real part describes the pressure field while the imaginary part represents the streamlines of the flow. The potential (1) can be differentiated to obtain a flow field $$\overline{u} = \frac{d\Phi}{dz} = u_x - iu_y.$$

It has the significant advantage to enable the use of conformal mapping, a complex analysis technique which enables the transformation of the solution of specific 2D differential equations in a simple geometry into any solution of more complex geometries with an appropriate warping of the solution domain via a complex variable transformation of the form $\omega=f(z)$.

The approach then involved incorporating diffusive transport of diluted species in multipolar flow, and solving exactly the concentration profile in a Hele-Shaw system as described by the steady-state convection-diffusion equation under potential 2D flow $$\nabla^2 c - Pe\nabla\Phi \cdot \nabla c = 0 \quad (2)$$

where Pé is a known parameter to persons skilled in the art of transport modeling, which represents the ratio of diffusion to convection characteristic transport times within the device. The main difficulty in solving this equation comes from the algebraic term $\nabla\Phi \cdot \nabla c$, which quickly renders the equation intractable even for relatively simple flow patterns. In the case of multipolar flows, an additional difficulty arises from the fact that the flow profile contains singularities within the solution domain (at the openings) which further complicate the problem and make the definition of correct boundary conditions for the equation non-trivial. To get around that issue, conformal invariance of the convection-diffusion equation in transport problems involving potential flows are used, based on a premise that the same transformations that can be used in solving the convection problem can be applied to the diffusion problem as well. The method rests upon solving convection-diffusion in streamline coordinates ($\phi=\text{Re}\{\Phi\}$, $\psi=\text{Im}\{\Phi\}$), then using the complex potential to transform the solution back and obtain the complete diffusion profile. In the streamline domain, the flow reduces to a simple straight flow and convection becomes decoupled from diffusion, which makes the problem considerably simpler. The convection-diffusion equation then simply becomes $$\frac{\partial^2 c}{\partial \phi^2} + \frac{\partial^2 c}{\partial \psi^2} = Pe\frac{\partial c}{\partial \phi} \quad (3)$$

The singularities correspond to the injection and aspiration apertures and thus are an important part of the flow that cannot be hidden away. Additionally, the fact that the footprint of the dipolar probe is itself a finite shape may cast doubt on the possibility of finding an analytical solution, as analytical expressions exist only for semi-infinite absorbers. Nevertheless, this exact solution is obtained as shown below.

Using the change of variable described above, the advection diffusion profile under a dipole flow can be represented easily in dimensionless units, with an injection aperture (c=1) located at the origin and an aspiration aperture (c=0) at z=−1. The ratio of aspiration to injection flow rates is given by the parameter $$\alpha = \frac{q_{asp}}{q_{inj}} > 1.$$

The flow pattern in such a probe has a well known stagnation point located at $$z_{stag} = \frac{1}{\alpha - 1} \quad (4)$$

The concentration at the stagnation point, as well as on the segment of streamline connecting the stagnation point to the aspiration aperture, is necessarily c=½ due to the problem's inversion symmetry. Furthermore, upon inspection, the problem can be transformed to streamline coordinates using the function $$\Phi(z)=\log(z)-\alpha \log(z+1) \quad (5)$$

In the streamline domain $\Phi$, the separating line going from the stagnation point to the aspiration aperture becomes a semi-infinite segment of the horizontal axis at fixed concentration c=½. The problem of convection-diffusion around such a semi-infinite obstacle has been extensively studied in fluid mechanics, notably in the theory of dendrite solidification, and has the solution $$c(\Phi)=\tfrac{1}{2}(1\pm erf(Im\sqrt{Pe(\Phi-\Phi_{stag})})) \quad (6)$$

where $\Phi_{stag}$ is the image of the stagnation point, erf(x) is the error function (cit Lebedev or Abramowitz' function book). The sign of ± is determined by whether we have an incoming flow of concentration c=0 or c=1. However, neither of these concentration profiles represent the full dipole footprint when transformed. This can be seen physically in the dipolar probe flow, in which there is both incoming fluid at concentration 0 (aspirated from the probe's surroundings), and incoming fluid at concentration 1 (injected by the aperture). To solve this issue, the problem is separated into an "interior" and an "exterior" domain, separated by the line of concentration ½. There remains an ambiguity due to the branch cut of the logarithm functions in (1), but the branch cut is avoided by having the singularities on the horizontal axis and using it as an axis of symmetry.

The final step is then to obtain the entire solution as a piecewise function matching the "interior" and an "exterior"

solution, given by transforming (6) back to the dipole flow domain z. The interior and exterior domains can be defined either by checking the sign of Φ in the streamline domain or by using the expression for the separating line in the z domain in polar coordinates. This provides the complete, unique, and exact expression for the concentration profile in the dipolar probe $$c(z)=\tfrac{1}{2}(1\pm erf(Im\sqrt{Pe(\log(z)-\alpha\log(z+1)-\Phi_{stag})}))\qquad(7)$$

We note that this expression is valid for all values of the Péclet number.

Example 2—Expanding the Model to all Multipolar Devices

The dipolar probe concept was expanded to any multipolar device for an arbitrary number of injection and aspiration apertures arranged in different configurations to generate a variety of flow and diffusion patterns, using conformal transforms.

The transport problem is first solved in the streamline domain, then transformed to obtain the flow profile for a dipolar probe. The dipolar probe solution can then be transformed again to obtain an entire family of symmetrical multipolar displays. These devices will have injection and aspiration apertures located at new positions, determined by the transform of the initial aperture locations, and can then be fabricated and operated to obtain the predicted patterns. This method may allow the design of new configurations of microfluidic devices with predictable outcomes.

Using the transforms illustrated in Table 1, the concentration profile for fluid delivery devices can be obtained from the dipole solution without having to do any new calculations.

TABLE 1

Transform functions that can be applied to the dipole solution to obtain new design of fluid delivery devices

| | |
|---|---|
| Straight Flow | $\omega = \log(z) - \alpha \log(z+1)$ |
| Quadrupole | $\omega = (2z+1)^{1/2}$ |
| Flower Probe | $\omega = (z+1)^{1/n}$ |
| Polygonal Probe | $\omega = z^{1/n}$ |
| Impinging Flows | $\omega = \tfrac{1}{2}$ |

Finally, in order to apply conformal mapping to the advection diffusion equation under potential flow, any initial map (a 2D image of the diffusion profile) is used, may it be analytical, numerical, or even experimental. Thus, an initial numerical map from a finite element situation can be used as an initial "known solution" onto which conformal transforms are applied on the image to yield entirely new solutions, making the approach versatile and useful even in cases where no a priori analysis has been made.

Figure 21:
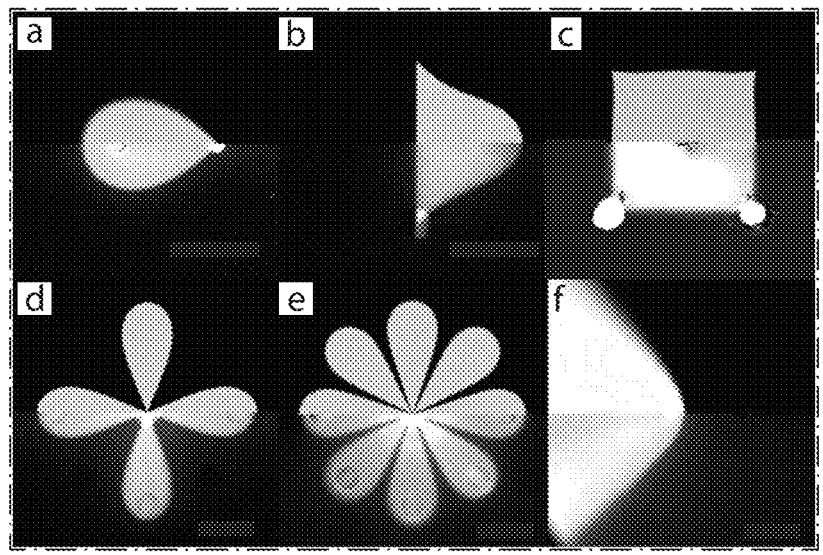
FIG. 21 is a comparison of surface fluid patterns obtained experimentally and through an analytical model as described in Example 2, according to certain embodiments of the present technology.

The theoretical models were compared to experimental models of the fluid delivery devices with the investigated configurations. A near perfect correspondence between the two was observed, thereby validating the theoretical model (FIG. 21).

Example 3—Fluid Delivery Device with Hexagonal Polygon Surface Opening Unit

A system comprising the fluid delivery device 20 having the surface opening unit 84 arrangement of the FIGS. 9, 12 and 13 was provided.

A single fluid was used and comprised fluorescein dissolved in an immersion medium. Regions of interest, shown as a white rectangle in FIG. 22a) were alternately and periodically exposed to the fluid. A "flower-like" surface fluid pattern 82 was obtained having a plurality of elements 90 in the shape of petals.

Figure 22:
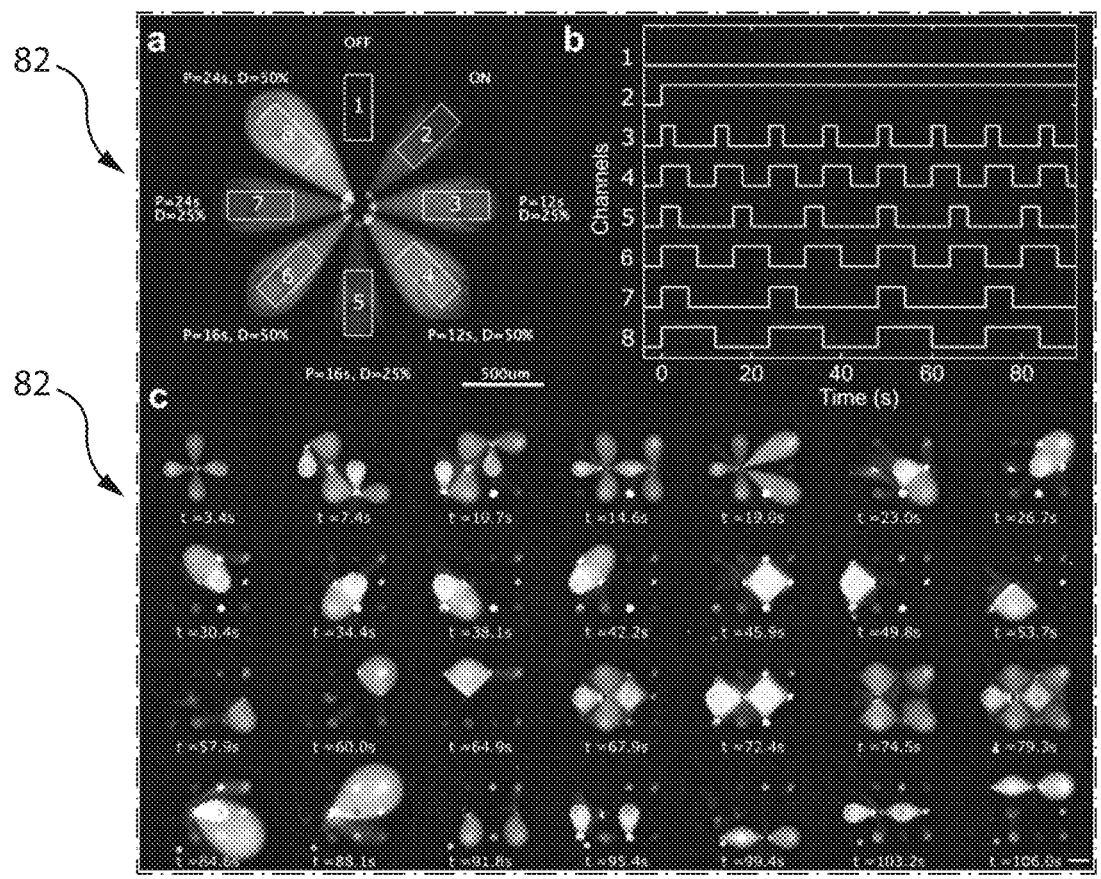
FIG. 22 shows surface fluid patterns obtained experimentally as described in Example 3, according to certain embodiments of the present technology.

Each petal 90 was exposed to a different periodical pattern with one petal 90 always exposed to the fluid, one never exposed, and the remaining six petals exposed to three different frequencies (period of 12 s, 16 s and 24 s) with two different duty cycles (25% and 50%). For each element 90, the amplitude (given by the reagent concentration), the frequency and the duty cycle of several chemical pulses could all be controlled independently (FIG. 22b). A transition time of <1 s was observed. This experiment used periods of tens of seconds to demonstrate fast reconfigurability, but periods, in the order of minutes and hours, more adapted to most biological process, could also be used. Confocal microscope was used as the imaging device.

It was found that the "flower-like" surface fluid pattern 82 obtained is capable of generating a large number of independent fluid conditions (N−1) with the minimum number of surface openings 26. Furthermore, each of the pixels 90 in the shape of the flower petals (i.e. the confined areas) could be kept stable by compensating for flow variations while surface openings 26 of the surface opening unit 84 are modulated between the open and closed modes. Such a surface opening unit 84 where modulation between the open and closed modes is possible can be considered as a stroboscope (or "c-strobe"), enabling the generation of a sequence of fluid surface patterns 82. Independent spatiotemporal control of fluid pulses, having the same or different configuration, on any given surface (such as the fluid transfer surface 70) can be achieved.

The width of each petal element 90 can be controlled by the number of surface openings within the surface opening unit 84 that can be turned on and off at any given time. Fixed-size elements 90 and thus independent confinement areas were achieved by tuning in real time the flow intensity in each of the openings according to the exact flow model described in Examples 1 and 2.

More specifically, the advection-diffusion solution of the surface opening unit 84 with only one surface opening turned on is the microfluidic dipole solution. When a second surface opening is added, advection diffusion of an element 90 follows a similar solution, the dipole solution, but compressed in half the complex plane. This results in a compressed element 90 width. The same effect applies to every number of surface openings 26. The advection-diffusion in the element 90 of an 8-petal surface opening unit 84 follows the dipole solution but compressed in one eighth of the complex plane. By changing the value of alpha to compensate the width compression for each number of petals turned on, the width can be kept constant.

Example 4—Immunofluorescent Assay Using the Fluid Delivery Device of Example 3

One use of fluid surface patterning is to perform immunoassays. Existing immunoassay techniques involve the sequential exposure of a tissue sample to various reagents as biomarkers. This can be a time intense process.

The fluid delivery device of Example 3 was used to demonstrate its use for in which a tissue sample could be concurrently exposed to different reagents.

Figure 23:
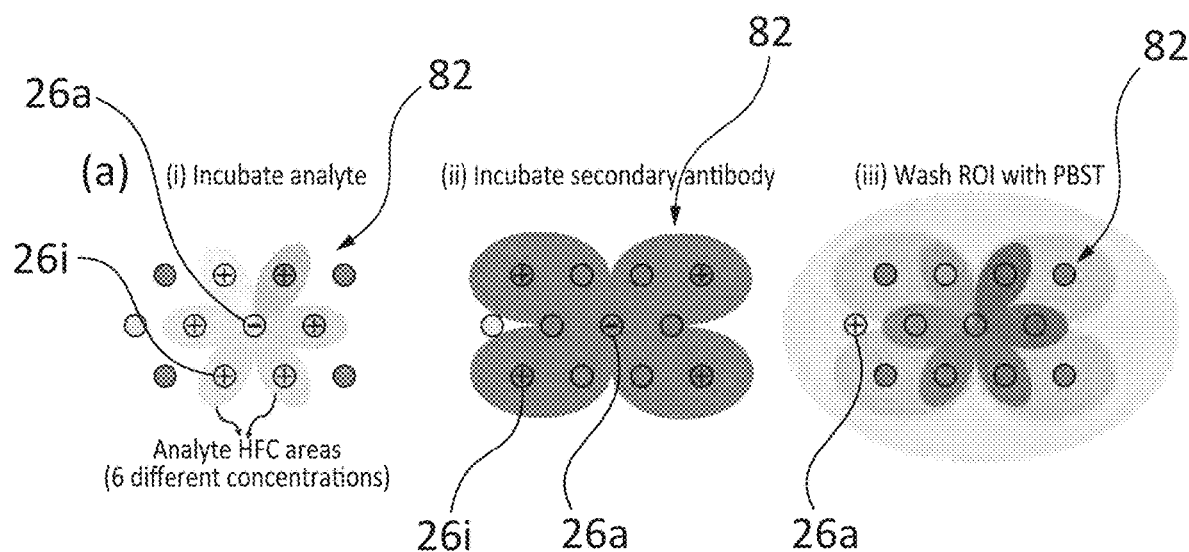
FIG. 23 is a schematic illustration of a use of the system of FIG. 1 as described in Example 4, according to certain embodiments of the present technology.

A fully automated three-step immunoassay using the staggered display 80 of FIG. 8 was performed (FIG. 23). Slides functionalized with capture antibodies were provided as the fluid transfer surface 70. The display 80 was first used to incubate six different concentrations of antigen, using a surface opening unit 84 comprising six injection openings 26*i* around an aspiration opening. A flower-like surface fluid pattern 82 was obtained (FIG. 23*a*(*i*)). After an incubation period of 50 min, the antigen injection apertures were stopped and the four corner surface openings outside of the previous injection openings 26*i* were used to inject fluorescently-labeled secondary antibodies over the previously exposed antigen zone for one hour (FIG. 23*a*(*ii*)). At the end of the secondary antibody incubation time, the fluid flow injections were stopped for 10 seconds to aspirate the secondary antibody between the display 80 and the surface 70. The central aspiration opening was then turned off, and an injection opening positioned outwardly of two of the four corner injection openings was used to inject PBST to wash the slide for 15 min (FIG. 23*a*(*iii*)). Operator manipulation of the slide was not required during the three steps.

The operator then removed the slide, dipped it in water and dried it using a nitrogen stream.

Figure 24:
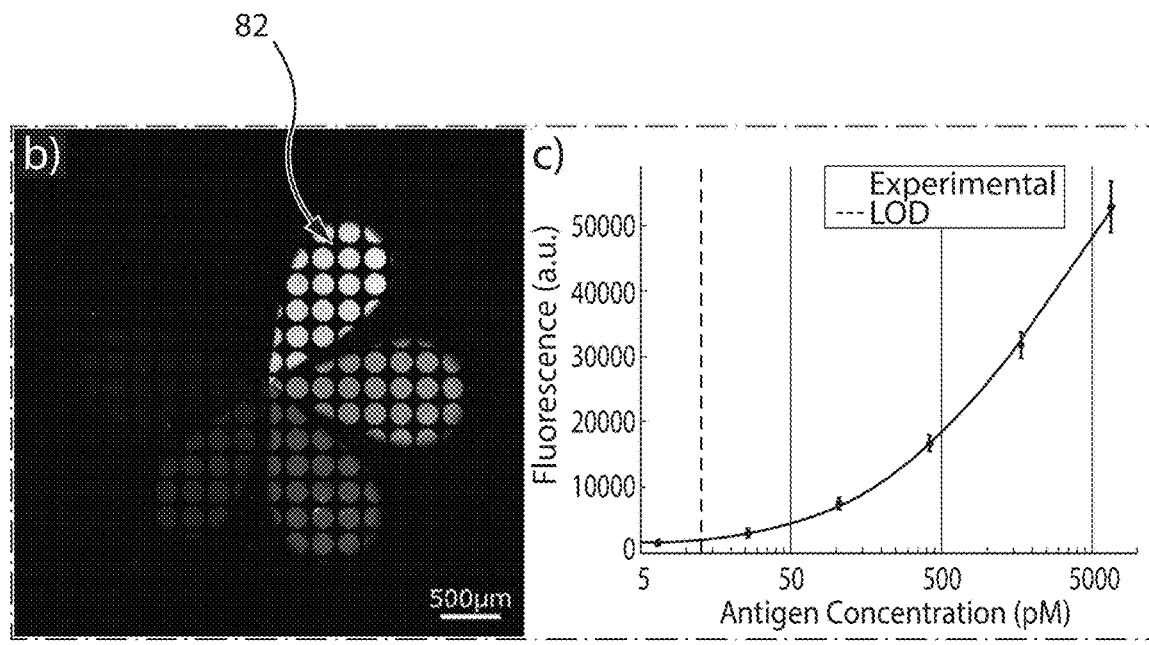
FIG. 24 shows experimental result obtained using an embodiment of the system of FIG. 1, described in Example 4, according to certain embodiments of the present technology.

Fluorescent images of the slides and the resulting binding curves are represented in FIG. 24. Confinement areas are well defined and show no sign of contamination between them. The experiment also demonstrates required confinement pattern stability for experiments in a timeframe of hours. In the presented binding curve (FIG. 23*c*), the area unstained by antigen but stained by secondary antibodies was considered as a control (Cantigen=0) as previous experiments showed that, as expected, a HFC area with [Cantigen]=0 give similar result to the secondary antibody stained background. The total volume of reagent was used over the whole experiment.

It will be appreciated that this example could be adapted for use with other displays 80 and using other surface opening units 84. Instead of the reagents used in the example and the processing steps, the method 200 and system 10 could be adapted for other processing steps and reagents.

Advantageously, unlike "closed" microfluidic systems where different conditions are tested in different chambers and channels, using embodiments of the present technology, factors such as biological variations, errors in human handling of the system or variation of temperature can be avoided or minimized.

Example 5—Comparison Between an Embodiment of the Fluid Delivery Device of the Present Technology and a Dipolar Probe for Surface Patterning FIG. 25*a* illustrates a dipolar probe experiment to produce a fluid surface pattern and FIG. 25*b* illustrates how an embodiment of the fluid delivery device 20 (FIG. 15) could be used to achieve the same experiment in a quicker way. In this report, the conventional dipolar probe is used to locally stain a tissue section with anti-P53 antibodies, anti-PR antibodies and hematoxylin. As only one reagent can be patterned at once, the dipolar probe is used to pattern a line of hematoxylin by scanning the probe on the surface (FIG. 25*a*1). Then, the reagent is changed and the probe pattern spot of anti P53 with patterning time of few hundred seconds by spots (FIG. 25*a*2). The reagent is changed again and anti-PR is used to pattern another spot on the surface (FIG. 25*a*3).

Figure 25:
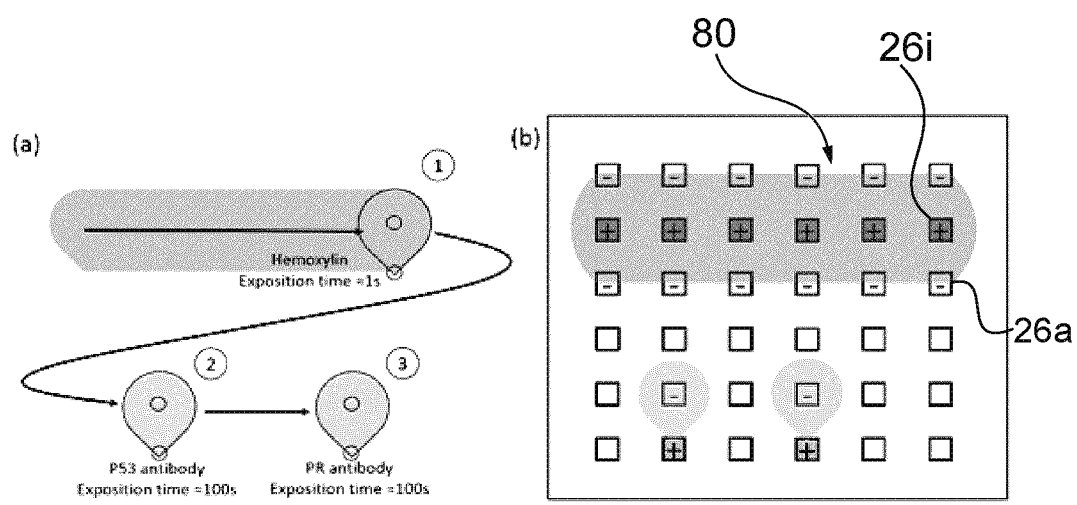
FIG. 25 is a schematic illustration of a comparison of a use of an embodiment of the system of FIG. 1 and a dipolar probe, described in Example 5.

Using the fluid delivery device 20 having the display 80 of FIG. 15, the hematoxylin line and multiple spots of anti-PR and anti-P53 antibodies could be patterned concurrently (FIG. 25 *b*). As the exposure time is long (few hundred second), exposing multiple reagent simultaneously saved time. The more different areas and stains are to be tested, the more the reagent display is advantageous. Not having to change the injected reagent would also limit contamination risks and simplify the experiment for the user.

Example 6—Fluid Delivery Systems Including Manifolds

Fluid delivery systems 10 with different fluid delivery configurations were investigated, and particularly the use of manifolds 97.

Figure 26:
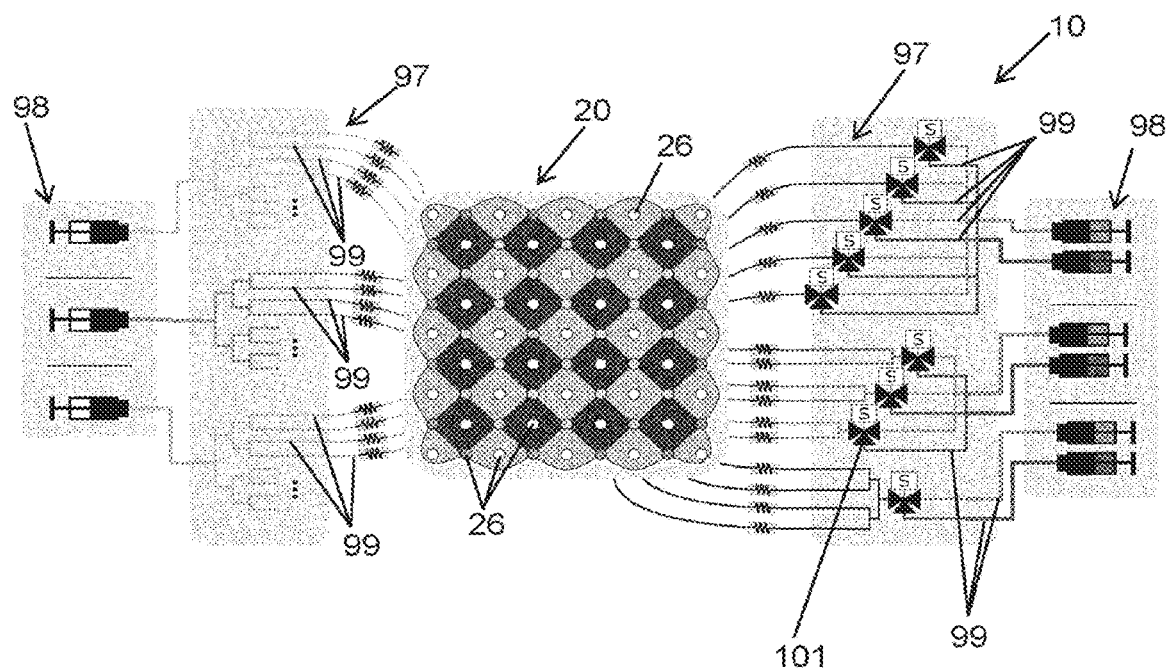
FIG. 26 is a schematic illustration of fluid delivery systems with manifolds, described in Example 6, according to certain embodiments of the present technology.
Figures 27A, 27B, 27C, 27D:
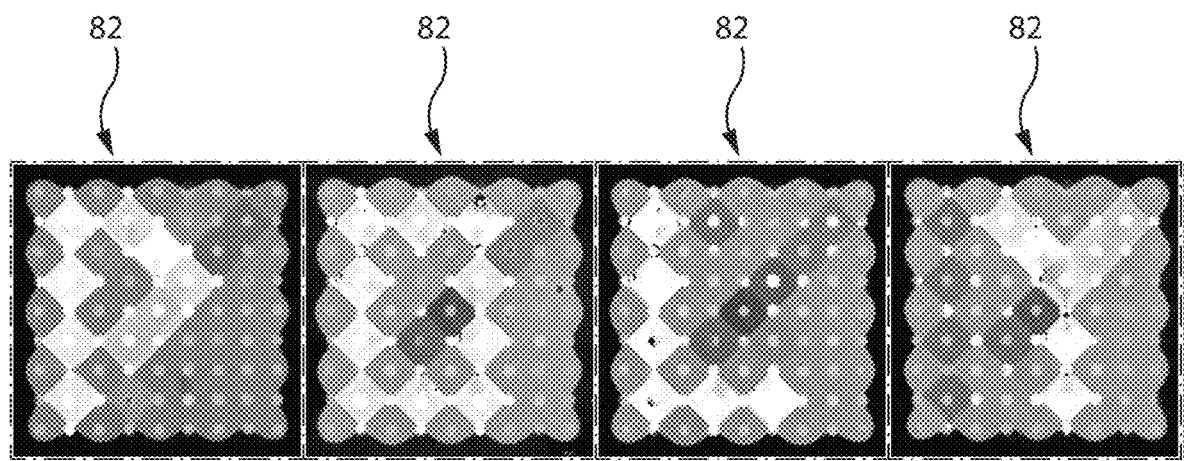
FIG. 27A-D are surface fluid patterns obtained experimentally using the fluid delivery systems of FIG. 26, according to certain embodiments of the present technology.

As seen in FIG. 26, on the left side is illustrated a manifold 97 arrangement in which a plurality of manifolds 97 are provided in fluid communication with a plurality of syringe pumps 98 (pump system 60 and fluid reservoir system 30). Each syringe pump 98 holds a fluid with a different phase (different colours) and has an associated manifold 97. The syringe pumps 98 can be programmable. Extending from each manifold 97 is a plurality of tubes 99 for delivering the fluid from the syringe pump 98 to the fluid delivery device 20 (via the manifold 97). Each tube 99 is associated with a given surface opening 26 of the fluid delivery device 20. Hydraulic resistors are provided on each tube.

On the right side of FIG. 26 is illustrated an alternative manifold 97 configuration in which each manifold 97 is in fluid communication with a plurality of syringe pumps 98 holding different fluids (e.g. different colour fluids). In this case, valves 101 are provided for additional control of the fluid flow and in particular for stopping and starting the fluid flow to the fluid delivery device 20.

Figure 28A:
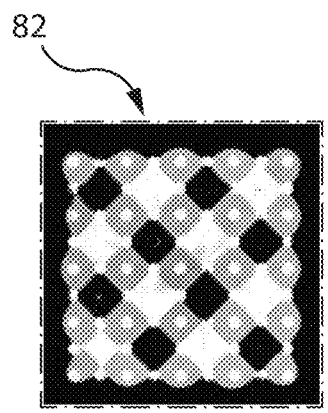
FIG. 28A-C are further surface fluid patterns obtained experimentally using the fluid delivery systems of FIG. 26, according to certain embodiments of the present technology.
Figure 28B:
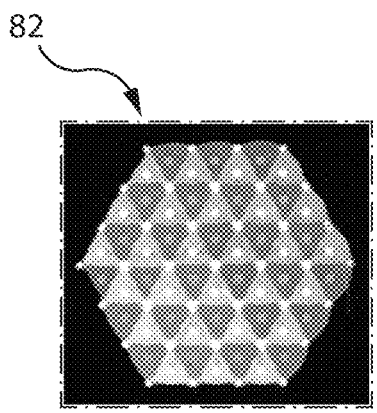
Figure 28C:
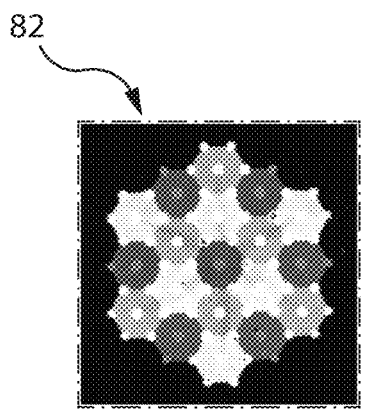
Figures 29A, 29B:
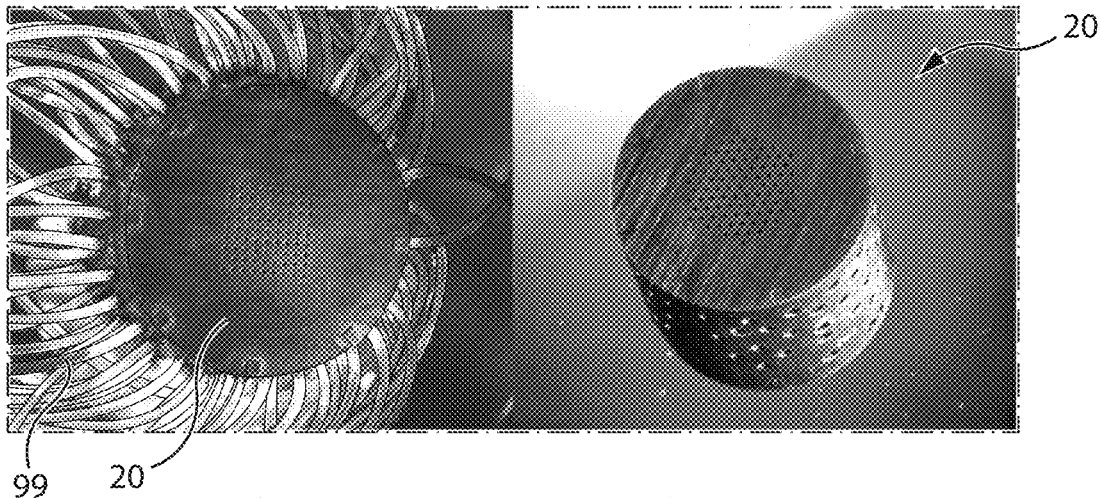
FIGS. 29A and 29B show fluid delivery devices having more than 80 surface openings, according to certain embodiments of the present technology.
Figure 30:
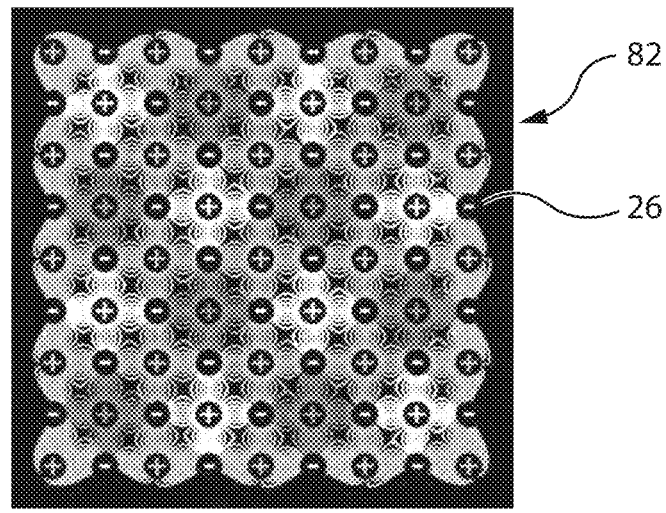
FIG. 30 illustrates schematically the fluid flow direction for a given surface pattern that can be achieved with fluid confinement, according to certain embodiments of the present technology.
Figure 31:
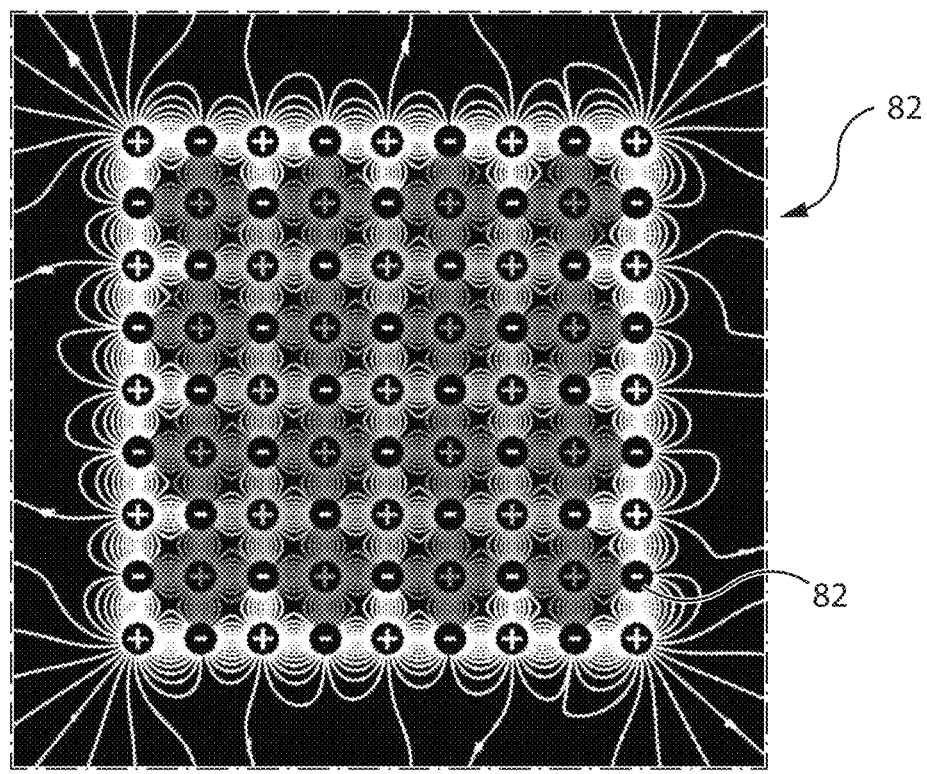
FIG. 31 illustrates schematically the fluid flow direction for a given surface pattern that can be achieved without fluid confinement, according to certain embodiments of the present technology.
Figures 32A, 32B, 32C:
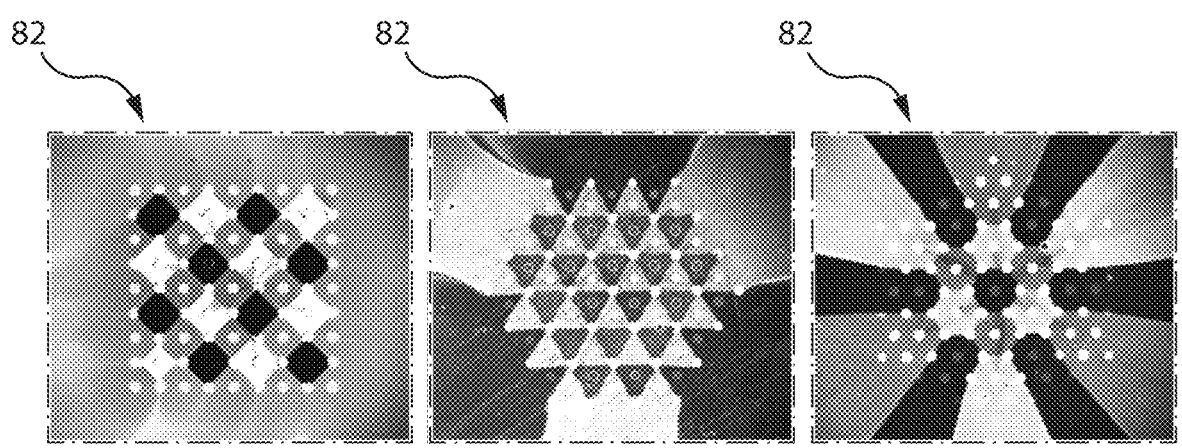
FIGS. 32A-C illustrates surface fluid patterns obtained experimentally using the fluid delivery systems without fluid confinement according to certain embodiments of the present technology.

The use of manifolds 97 and valves 101 can enable the implementation of fluid delivery devices 20 that have any required number and arrangement of surface openings 26 formed therein (see for example FIGS. 29A and 29B), and enable the formation of many different fluid surface patterns 82 and surface pattern sequences (see for example FIGS. 27A-D, and FIGS. 28B-C). More specifically, different fluid surface patterns 82 can be created using the same aperture array geometry. In FIGS. 27A-D and FIG. 28A a square aperture array is utilized, and in FIGS. 28 B-C, a staggered aperture array is used. In FIGS. 28 and 32, the scale bar indicates 1 mm. Arrays of more than hundreds of surface openings 26 are possible. FIG. 30 illustrates schematically the fluid flow direction for a given surface pattern 82 that can be achieved with fluid confinement (wet fluid delivery surface 70), and FIG. 31 illustrates schematically the fluid flow direction for a given surface pattern 82 that can be achieved without fluid confinement (dry fluid delivery surface 70). FIG. 32 illustrates example fluid surface patterns 82 achieved with no fluid confinement.

It should be expressly understood that not all technical effects mentioned herein need to be enjoyed in each and every embodiment of the present technology.

Modifications and improvements to the above-described implementations of the present technology may become apparent to those skilled in the art. For example, alternative transverse adjustment mechanisms and longitudinal adjustment mechanisms are possible. The foregoing description is intended to be exemplary rather than limiting. The scope of the present technology is therefore intended to be limited solely by the scope of the appended claims.

The invention claimed is:

1. A system of fluid delivery for providing a surface fluid pattern, the system comprising:
   a fluid delivery head;

a fluid reservoir system for supplying fluid to the fluid delivery head and/or for receiving fluid from the fluid delivery head;

the fluid delivery head having at least one fluid delivery port fluidly connected to the fluid reservoir system for fluid flow to and from the fluid delivery head, the fluid delivery head comprising:

a body having a fluid delivery surface which is planar and on which can be formed the surface fluid pattern, the fluid delivery surface having a plurality of surface openings defined therein, the plurality of surface openings being arranged across the fluid delivery surface as a two-dimensional array;

each surface opening of the plurality of surface openings being fluidly connected to the at least one fluid delivery port for fluid flow to and from each surface opening;

a pump system for modulating the fluid flow to and from the fluid delivery head such that fluid can flow through a given surface opening as an injection or an aspiration of fluid; and a computer system comprising a processor, the processor being communicatively coupled to the pump system and configured to execute a method to create the fluid surface pattern on the fluid delivery surface, the method comprising:

causing fluid to be aspirated away from the fluid delivery surface through at least three adjacent surface openings of the plurality of surface openings; and causing fluid to be injected towards the fluid delivery surface through another surface opening of the plurality of surface openings which is positioned inwardly of the at least three surface openings.

2. The system of claim 1, wherein the another surface opening through which there is fluid injection and the at least three adjacent surface openings through which there is fluid aspiration comprises a surface opening unit, there being a plurality of the surface opening units of the plurality of surface openings, and wherein the processor is configured to modulate fluid flow through the plurality of surface opening units, to form a repeating fluid surface pattern across the fluid delivery surface.

3. The system of claim 1, wherein the fluid delivery head includes one or more protrusions on the fluid delivery surface for spacing the fluid delivery surface from a fluid transfer surface.

4. The system of claim 1, wherein the pump system comprises at least one pump fluidly connected to the plurality of surface openings through the at least one fluid delivery port of the fluid delivery head.

5. The system of claim 1, wherein the processor is further configured to control a fluid parameter of the fluid through the plurality of surface openings, the fluid parameter comprising one or more of:
a fluid flow rate,
a fluid volume,
a fluid flow duration,
a flow of a fluid phase,
a flow of a fluid concentration,
a fluid flow cycle,
a fluid flow frequency, wavelength or time, and
a fluid flow concentration gradient.

6. The system of claim 1, wherein the reservoir system comprises a first reservoir and a second reservoir, the first reservoir storing a fluid having a different property than fluid stored in the second reservoir.

7. The system of claim 1, wherein the fluid delivery head includes a plurality of channels, each channel fluidly connecting a respective surface opening and a respective fluid delivery port.

8. The system of claim 1, wherein the two-dimensional array of the plurality of surface openings comprises the surface openings being positioned along parallel rows, in which the surface openings of each adjacent row are either aligned or staggered.

9. The system of claim 1, further comprising at least one valve for modulating fluid flow to the plurality of surface openings, the processor communicatively connected to the at least one valve to control the at least one valve.

10. The system of claim 1, wherein the two-dimensional array of the plurality of surface openings has one or more of a translational symmetry, a rotational symmetry or an inversion symmetry.

11. The system of claim 1, wherein the two-dimensional array of the plurality of surface openings comprises a repeating pattern of surface opening units, wherein the repeating pattern has symmetry on two or more planes.

* * * * *